United States Patent [19]

Mahadevan-Jansen et al.

[11] Patent Number: 5,842,995
[45] Date of Patent: Dec. 1, 1998

[54] SPECTROSCOPIC PROBE FOR IN VIVO MEASUREMENT OF RAMAN SIGNALS

[75] Inventors: Anita Mahadevan-Jansen; Rebecca Richards-Kortum, both of Austin; Michele Follen Mitchell, Houston, all of Tex.

[73] Assignee: Board of Regents, The Univerisity of Texas System, Austin, Tex.

[21] Appl. No.: 672,623

[22] Filed: Jun. 28, 1996

[51] Int. Cl.⁶ ........................................... A61B 6/00
[52] U.S. Cl. ............................... 600/473; 600/476
[58] Field of Search .................... 128/664, 665, 128/658, 772; 600/110, 129, 160, 167, 181, 182, 473, 475, 476, 478, 342; 607/88, 92

[56] References Cited

U.S. PATENT DOCUMENTS

| | | |
|---|---|---|
| 1,643,718 | 9/1927 | Loeck . |
| 4,556,057 | 12/1985 | Hiruma et al. ................ 128/303.1 |
| 4,648,892 | 3/1987 | Kittrell et al. .................. 65/4.21 |

(List continued on next page.)

FOREIGN PATENT DOCUMENTS

| | | | |
|---|---|---|---|
| 0 608 987 A1 | 8/1994 | European Pat. Off. ..... | G01N 33/574 |
| 1151436 | 6/1989 | Japan ............... | A61R 5/00 |
| WO 88/05908 | 8/1988 | WIPO ............... | G01N 15/14 |
| WO 95/26673 | 10/1995 | WIPO ............... | A61B 5/00 |

OTHER PUBLICATIONS

Alfano et al., "Human Breast Tissues Studies by IR Fourier Transform Raman Spectroscopy," *Lasers in the Life Sciences*, 4(1):23–28, 1991

Angel et al., "Computer–Controlled Instrument for the Recovery of a Resonance Raman Spectrum in the Present of Strong Luminescence," *Anal. Chem.*, 56, 3000–3001, 1984.

Baraga *et al.*, "In situ Optical Histochemistry of Human Artery Using Near Infrared Fourier Transform Raman Spectroscopy, "*Proc. Natl. Acad. Sci.*, 89:3473–3477, 1992

Bot et al., "Raman Microspectroscopy of Fixed Rabbit and Human Lenses and Lens Slices: New Potentials," *Exp. Eye Res.*, 49:161–169, 1989.

Brennan et al., "In situ Histochemical Analysis of Human Coronary Arteries by Raman Spectroscopy Compared with Biochemical Assay,"In *Advances in Fluorenscence Sensing Technology*, vol. II., ed. J.R. Lakowicz, SPIE Proceedings 2388:105–109, 1995.

Clarke et al.,"Laser Raman Spectroscopy of Calcified Atherosclerotic Lesions in Cardiovascular Tissue," *Applied Optics*, 26(16):3175–3177, 1987.

Feld et al., "Detection and Characterization of Human Tissue Lesions with Near Infrared Raman Spectroscopy," *SPIE,*2388:99–104, 1995.

Frank et al., "Raman Spectroscopy of Normal and Diseased Human Breast Tissues," *Analytical Chemistry*, 67(5):777–783, 1995.

Frank et al., "Characterization of Human Breast Biopsy Specimens with Near–IR Raman Spectroscopy," *Anal. Chem.*, 66:319–326, 1994.

Funfschilling and Williams, "CW Laster Wavelength Modulation in Raman and Site Selection Fluorescence Spectroscopy," *Applied Spectroscopy*, , 30(4):443–446, 1976.

Keller et al., "Appliction of Near–Infrared–Fourier Transform Raman Spectroscopy in Medical Research, "*J. Raman Spectrosc.*, 25:663–671, 1994.

Kramer et al.,"Spectral Diagnosis of Human Coronary Artery: A Clinical System for Real Time Analysis, " *SPIE*, 2395:376–382, 1995.

(List continued on next page.)

*Primary Examiner*—Marvin M. Lateef
*Assistant Examiner*—Shawna J. Shaw
*Attorney, Agent, or Firm*—Arnold, White & Durkee

[57] ABSTRACT

An optical probe is disclosed which is suitable for rapidly measuring Raman spectra in vivo. The probe is designed to minimize interfering Raman and fluorescence signals generated within the probe itself. In addition, the probe design is compact, making it particularly suited for use in confined spaces such as body cavities. In one embodiment, the probe is employed to detect tissue abnormalities such as cervical cancers and precancers.

39 Claims, 14 Drawing Sheets

U.S. PATENT DOCUMENTS

| | | | |
|---|---|---|---|
| 4,675,529 | 6/1987 | Kushida | 250/458.1 |
| 4,755,684 | 7/1988 | Leiner et al. | 250/461.1 |
| 4,760,839 | 8/1988 | Nagasaki . | |
| 4,768,513 | 9/1988 | Suzuki | 128/634 |
| 4,785,814 | 11/1988 | Kane . | |
| 4,786,813 | 11/1988 | Svanberg et al. | 250/461.1 |
| 4,913,142 | 4/1990 | Kittrell et al. | 606/7 |
| 4,930,516 | 6/1990 | Alfano et al. | 128/665 |
| 4,967,745 | 11/1990 | Hayes et al. | 128/303.1 |
| 4,987,884 | 1/1991 | Nishioka et al. . | |
| 5,003,977 | 4/1991 | Suzuki et al. | 128/633 |
| 5,009,655 | 4/1991 | Diagnault, Jr. et al. | 606/7 |
| 5,014,707 | 5/1991 | Schwarz et al. | 128/633 |
| 5,026,368 | 6/1991 | Adair | 606/15 |
| 5,034,010 | 7/1991 | Kittrell et al. | 606/15 |
| 5,036,853 | 8/1991 | Jeffcoat et al. | 128/634 |
| 5,042,494 | 8/1991 | Alfano | 128/665 |
| 5,062,431 | 11/1991 | Potter | 128/665 |
| 5,078,711 | 1/1992 | Kakami et al. | 606/16 |
| 5,092,331 | 3/1992 | Nakamura et al. | 128/634 |
| 5,104,392 | 4/1992 | Kittrell et al. | 606/15 |
| 5,106,387 | 4/1992 | Kittrell et al. | 606/15 |
| 5,125,404 | 6/1992 | Kittrell et al. | 128/634 |
| 5,131,398 | 7/1992 | Alfano et al. | 128/665 |
| 5,192,278 | 3/1993 | Hayes et al. | 606/15 |
| 5,199,431 | 4/1993 | Kittrell et al. | 128/634 |
| 5,201,318 | 4/1993 | Rava et al. | 128/665 |
| 5,251,613 | 10/1993 | Adair | 128/6 |
| 5,261,410 | 11/1993 | Alfano et al. | 128/664 |
| 5,280,788 | 1/1994 | Janes et al. | 128/665 |
| 5,290,275 | 3/1994 | Kittrell et al. | 606/15 |
| 5,303,026 | 4/1994 | Strobl et al. | 356/318 |
| 5,304,173 | 4/1994 | Kittrell et al. | 606/15 |
| 5,318,023 | 6/1994 | Vari et al. | 128/633 |
| 5,318,024 | 6/1994 | Kittrell et al. | 128/634 |
| 5,345,941 | 9/1994 | Rava et al. | 128/665 |
| 5,353,791 | 10/1994 | Tamura et al. | 128/633 |
| 5,377,676 | 1/1995 | Vari et al. | 128/634 |
| 5,408,996 | 4/1995 | Salb | 128/633 |
| 5,419,323 | 5/1995 | Kittrell et al. | 128/653.1 |
| 5,421,337 | 6/1995 | Richards-Kortum et al. | 128/665 |
| 5,421,339 | 6/1995 | Ramanujam et al. | 128/665 |
| 5,439,000 | 8/1995 | Gunderson et al. | 128/664 |
| 5,441,053 | 8/1995 | Lodder et al. | 128/664 |
| 5,450,125 | 9/1995 | Ulich et al. | 348/31 |
| 5,450,857 | 9/1995 | Garfield et al. | 128/778 |
| 5,452,723 | 9/1995 | Wu et al. | 128/664 |
| 5,467,767 | 11/1995 | Alfano et al. | 128/665 |
| 5,496,305 | 3/1996 | Kittrell et al. | 606/15 |
| 5,507,287 | 4/1996 | Placic et al. | 128/633 |
| 5,552,134 | 9/1996 | Morgan et al. | 424/9.61 |
| 5,590,660 | 1/1997 | MacAulay et al. . | |
| 5,608,520 | 3/1997 | Fleming . | |

OTHER PUBLICATIONS

Lewis et al., "Raman Spectrometry and Neural Networks for the Classification of Wood Types–1," *Spectrochimica Acta*, 50A(11):1943–1958, 1994.

Liu et al., "Raman,Fluorescence and Time–Resolved Light Scattering as Optical Diagnostic Techniques to Separate Diseased and Normal Biomedical Media," J. Photochem. Photobiol. B: Biol., 16:187–209, 1992.

Liu *et al.,* "Near–IR Fourier Transform Raman Spectroscopy of Norman and Athersclerotic Human Aorta,"*Lasers in the Life Sciences,* 4(3):257–264, 1992.

Mahadevan et al., "Optical Techniques for the Diagnosis of Cervical Precancers: A Comparison of Raman and Fluorescence Spectroscopies," *SPIE,*2388:110–120,1995.

Manoharan et al. "Ultraviolet Resonance Raman Spectroscopy for Detection of Colon Cancer," *Lasers in Life Sciences,*6:217–227, 1995.

Manoharan et al.,"Raman Spectroscopy for Cancer Detection: Instrument Development and Tissue Diagnosis," *SPIE,* 2328, 128–132, 1994.

Mizumo et al.,"Near–Infrared Fourier Transform Raman Spectroscopic Study of Human Brain Tissues and Tumours, "*J. Raman Spectrosc.,*25–25–29, 1994.

Mosier–Boss et al.,"Fluorescence Rejection in Raman Spectroscopy by Shifted–Spectra, Edge Detection, and FFT Filtering Techniques," *Applied Spectroscopy,* 49(5):630–638, 1995.

Myrick et al.,"Comparison of Some Fiber Optic Configurations for Measurement of Luminescence and Raman Scattering," *Applied Optics,*s29(9):1333–1344, 1990.

Myric and Angel, "Elimination of Background in Fiber–Optic Raman Measurements,"*Applied Sectroscopy,* 44(4):565–570,1990.

Nie et al., "Applications of Near–Infrared Fourier Transform Raman Spectroscopy in Biology and Medicine," *Spectroscopy,* 5(7):24–32, 1990.

Ozaki, "Medical Application of Raman Spectroscopy," *Applied Spectroscopy Reviews,*24(3 & 4):259–312, 1988.

Ozaki et al., "Biomedical Application of Near–Infrared Fourier Transform Raman Spectroscopy, Part I: The 1064–nm Excited Raman Spectra of Blood and Met Hemoglobin," *Applied Spectroscopy,* 46(3):533–536, 1992.

Palcic et al., "Detection and Localization of Early Lung Cancer by Imaging Techniques," *Chest,*99:742–743, 1991.

Puppels et al., "Laser Irradiation and Raman Spectroscopy of Single Living Cells and Chromosomes: Sample Degradation Occurs With 514.5 nm but Not With 660 nm Laser Light," *Experimental Cell Research,*195(2):361–367, 1991.

Puppels et al., "Raman Microspectroscopic Approach to the Study of Human Granulocytes," *Biophys. J.,* 60:1046–1056, 1991.

Redd et al., "Raman Spectroscopic Characterization of Human Breast Tissues: Implications for Breast Cancer Diagnosis,"Applied Spectroscopy, 47(6):787–791, 1993.

Schrader et al.,"NIR FT Raman Spectroscopy in Medical Diagnosis," *Journal of Molecular Structure,*348:293–296, 1995.

Schwab and McCreery, "Versatile, Efficient Raman Sampling with Fiber Optics,"*Anal., Chem.,*56:2199–2204, 1984.

Shreve et al.,"Effective Rejection of Fluorescence Interference in Raman Spectroscopy Using a Shifted Excitation Difference Technique," *Applied Spectroscopy,* 46(4):707–711, 1992.

Van Duyne et al.,"Mode–Locked Laser Raman Spectroscopy–A New Technique for the Rejection of Interfering Background Luminescence Signals," *Anal. Chem.,* 46(2):213–222, 1974.

Williams and Barry, "Comparison of Fourier Transform Raman Spectra of Mammalian and Reptilian Skin,"*Analyst,* 119:563–566, 1994.

Williams et al.,"A Critical Comparison of Some Raman Spectroscopic Techniques for Studies of Human Stratum Corneum," *Pharmaceutical Research,*10(11):1642–1647, 1993.

Yu et al., "Disulfide Bond Formation in the Eye Lens," *Proc. Natl., Acad. Sci. USA,*82:7965–7968, 1985.

Yu et al.,"Laser Raman Spectroscopy of the Lens in–situ Measured in an Anesthetized Rabbit," *Curr. Eye Res.,* 1(10):615–618, 1981–1982. Abstract only.

SPECTROSCOPIC PROBE FOR IN VIVO MEASUREMENT OF RAMAN SIGNALS

BACKGROUND OF THE INVENTION

1. Field of the Invention

The invention relates to a device for detecting Raman spectra from tissue samples in vivo. In particular, the probe is designed to emit electromagnetic radiation in the near-IR range, which will induce Raman emission spectra from tissue samples in a patient. These tissues may be suspected cancers or precancers, and their Raman emission spectra permit an estimation of their relative abnormality.

2. Related Art

Cervical cancer is the second most common malignancy among women worldwide. In 1995, it was estimated that 4,800 deaths will occur in the United States alone from this disease and 15,800 new cases of invasive cervical cancer will be diagnosed (1). Although early detection of cervical precancer has played a central role in reducing the mortality associated with this disease over the last 50 years (2), the incidence of pre-invasive squamous carcinoma of the cervix has risen dramatically, especially among women under the age of 35 (3). Existing screening and detection techniques, the Pap smear and colposcopy, have several deficiencies that prevent efficient management of an otherwise controllable disease. The primary screening tool is the Pap smear, which has a high false negative error rate of 15–40% due to sampling and reading errors (4). Colposcopy, which usually follows an abnormal Pap smear, requires extensive training and its accuracy is variable and limited even in the hands of expert practitioners (5). The mortality of cervical cancer among women under 50 years increased by 3% between 1986 and 1990, and this trend may continue unless further improvements are made in current detection techniques (6).

Recently, fluorescence, infrared absorption and Raman spectroscopes have been proposed for cancer and precancer screening and diagnosis (7–13). Many groups have successfully demonstrated the potential of spectroscopic techniques to improve diagnosis in various organ systems (7–22). Intrinsic tissue fluorescence has been used to differentiate normal and abnormal tissues in the human breast and lung (7), bronchus (8) and gastrointestinal tract (9). Fluorescence spectroscopy has been shown to be a promising technique for the clinical diagnosis of cervical precancer (10–12).

To further improve the diagnostic capability of spectroscopy for detection of cervical precancers, Raman spectroscopy has been considered. In comparison with fluorescence, Raman signals are weak and require sensitive instrumentation for detection. However, only a limited number of biological molecules contribute to tissue fluorescence, most with broadband emission. Many more molecules are Raman-active, with fingerprint spectra providing molecular specific information that can be applied to diagnose diseased tissue. As a result, in recent years, several groups have studied the potential of Raman spectroscopy for disease detection (13–21). Alfano et al. have used Fourier Transform Raman spectroscopy to detect gynecologic malignancies (16). Several groups have applied Raman spectroscopy to breast cancer detection (13, 18). Feld et al. have demonstrated the use of NIR and UV resonance Raman spectroscopy for identification of colon cancer and atherosclerosis (17, 19, 20).

Because most materials are Raman active, molecular-specific study of samples is possible. On the other hand, since most molecules are Raman active, the materials used in the Raman system themselves interfere with the detection of sample signal. Light typically is delivered using optical fibers made of silica in a remote sensing spectroscopic system. However, silica has a strong Raman signal which overrides sample signal. Glass, which transmits the near-infrared, has an intense fluorescence and Raman signal. However, UV grade silica (or quartz) has a much lower fluorescence and Raman signal and should preferably be used in a Raman system. The detected silica signal is generated in both the delivery and collection fibers used to measure tissue Raman spectra. A probe design should prevent this unwanted silica signal from being detected, as well as allow maximum collection of tissue Raman signal.

Several different designs have been proposed for clinical acquisition of Raman spectra using fiber optic probes (24, 25). In a breast tissue study, Frank et al. used two different fiber optic bundles: (i) a 6×1 fiber bundle accessible through a biopsy needle and (ii) an integrated 2×2 inch non-contact probe (DLT, Laramie, Wyo.), and tested it on breast tissue models and breast tissues in vitro (24). Fiber interference was found to be more significant for cancer samples with both probes due to reduced signal generation.

Berger et al. used a compound parabolic concentrator (CPC) at the distal tip of a probe with multiple collection fibers to yield signals with seven times more signal as compared to using a fiber probe without the CPC (25). Fiber background was reduced by using a dichroic mirror and separate excitation and collection fiber geometries. This probe design was used to acquire Raman spectra for transcutaneous blood glucose measurements. Although the potential application of a similar probe for coronary artery measurements were made, no further publications on its successful application have been found.

Other successful in vivo measurements have been in the eye (26), nail (27) and skin (28). Published reports of in vivo Raman applications have been confined to exposed tissue areas where fiber background could be circumvented using a macroscopic arrangement, e.g., DLT probe for breast tissues by Frank et al. (24) and CPC probe for transcutaneous measurements of blood analytes by Berger et al. (25). However, other organ sites such as the colon, cervix and oral cavity, require a more compact configuration and probe design. Thus, there clearly remains a need for improved optical probes capable of delivering near-IR electromagnetic radiation and detecting the resulting emission spectra in vivo.

SUMMARY OF THE INVENTION

It is an object, therefore, of the present invention to provide improved Raman spectroscopy probes for use in vivo. It also is an object to provide a probe suitable for use in a body cavity including, for example, the cervix. And it also is an object to provide a probe that has a minimal interfering Raman signal.

In satisfying these objects, there is provided an optical probe for in vivo examination comprising (a) a probe body having an optical opening at one end thereof, (b) an excitation leg disposed in the probe body, the excitation leg having an optical axis; (c) a collection leg disposed in the probe body, the collection leg having an optical axis; and (d) a mirror in operable relation to the optical axis of the excitation leg. In one embodiment, the excitation and collection legs are separate. Advantageously, the excitation leg is comprised of optical excitation fibers and the collection leg is comprised of optical collection fibers.

The excitation leg and the collection leg may be disposed longitudinally in said probe body, with parallel optical axes.

The mirror can be used to establish an optical path from the optical axis of the excitation leg to the optical opening. The optical opening may comprise air or a material that has a relatively low Raman signature, such as quartz, sapphire or transparent Teflon.

In more specific embodiments, the optical probe contains a focusing lens in the excitation leg. Also included in the excitation leg may be a filter, such as an interference filter, in operable relation to the focusing lens. The interference filter may be a bandpass filter, having a 3–4 mm diameter and blocking light with OD grater than about 5.

The optical probe may also contain a focusing lens in the collection leg, as well as a filter in operable relation to this focusing lens. The collection leg may advantageously employ a collimating lens in operable relation to the optical opening. An exemplary collimating lens would have a diameter of about 8 mm block light having an OD of greater than about 6. The collection leg filter may be a longpass filter or a notch filter. Advantageously, the notch filter is a holographic notch filter, having a diameter of about 8 mm. The number of collection fibers advantageously is 50, and the size of the collection fibers is 100 μm.

The mirror may be comprised of a polished gold wire. The polishing is advantageously conducted at a specific angle greater than the critical angle of quartz. Alternatively, the mirror is a parabolic mirror.

The probe may include an anodized interior, a diameter of less than 20 mm. The probe body may be comprised of carbonized epoxy or aluminum. Additionally, the probe body may be encased in heat-shrink tubing.

Another embodiment comprises an optical probe for in vivo examination comprising an elongated probe body having an optical window at one end thereof; an optical fiber disposed substantially longitudinally in the probe body, the optical fiber having first and second ends; an electromagnetic source coupler mounted on the probe body and coupled to the first end of the optical fiber; a first focusing lens disposed in the probe body and having an optical axis substantially normal to the second end of the optical fiber; an interference filter disposed in the probe body on the optical axis of the first focusing lens; a deflecting mirror disposed in the probe body on the optical axis of the first focusing lens, the interference filter being disposed between the first focusing lens and the deflecting mirror; an optical fiber bundle disposed substantially longitudinally in the probe body, the optical fiber bundle having first and second ends; an electromagnetic receiver coupler mounted on the probe body, the electromagnetic receiver coupler being coupled to the first end of the optical fiber bundle; a collimating lens disposed in the probe body and having an optical axis substantially normal to the second end of the optical fiber bundle; a holographic filter disposed in the probe body on the optical axis of the collimating lens and substantially normal thereto; and a second focusing lens disposed in the probe body and having an optical axis substantially normal to the second end of the optical fiber bundle, the holographic filter being disposed between the collimating lens and the second focusing lens; wherein the deflection mirror is angled with respect to the optical axis of the first focusing lens to establish an optical path from the optical axis of the first focusing lens that intersects with the optical axis of the second focusing lens in a region proximate to and outside of the probe optical window.

In still yet another embodiment, there is provided an apparatus for measuring Raman spectra in vivo comprising a probe according to claim 1; an electromagnetic radiation generator; a Raman spectrum detector; and a means for analyzing the spectra in relation to the electromagnetic radiation. The electromagnetic radiation generator preferably is a laser.

In still yet another embodiment, there is provided a method for collecting optical data from a sample site in vivo comprising generating excitation electromagnetic energy; conducting the excitation energy longitudinally through a probe; concentrating the excitation energy during the excitation energy conducting step; filtering the excitation energy during the excitation energy conducting step to eliminate all but a predetermined excitation wavelength from the excitation energy; deflecting the excitation energy following the concentration and filtering steps onto the sample site; conducting emission radiation resulting from the deflecting step longitudinally through the probe; expanding the emission radiation during the emission radiation conducting step; interference filtering the emission radiation during the emission radiation conducting step and after the expanding step to eliminate the excitation wavelength from the emission radiation; concentrating the emission radiation during the emission radiation conducting step and following the interference filtering step; and collecting the emission radiation following the concentrating step. In a particular embodiment, the probe comprises a window at an end thereof, the window having known fluorescence and Raman signatures, an the method further comprising bring the window into proximity with the tissue site during the collection step, and removing the known fluorescence and Raman signatures from the collected emission radiation.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specific embodiments presented herein.

FIG. 18A shows use of an algorithm employing a ratio of unnormalized intensities at 1656 cm$^{-1}$ and 1330 cm$^{-1}$ to separate SILs and non-SILs.

FIG. 18B shows use of an algorithm employing a ratio of unnormalized intensities at 1656 cm$^{-1}$ and 1454 cm$^{-1}$ to separate high grade and low grade SILs. ○ - normal; ◆ - inflammation; □ - metaplasia; ▲ - low grade SIL; ● - high grade SIL.

DETAILED DESCRIPTION OF THE INVENTION

A goal of the present inventors was to develop a probe capable of rapidly measuring Raman spectra in vivo without significant interference from materials used to construct the probe. Different probe designs were created to minimize fiber signal, leading to the development of a Raman probe which was successful in measuring Raman spectra in vivo. The advantages of the probe are its compact size, its relatively low Raman spectroscopic signature and its accuracy in measurement of Raman spectra in a short period of time. These advantages are as a result of a unique design that involves a series of microlenses and microfilters. The following detailed description is provided.

I. Raman Spectroscopy Probe for In vivo Use

The present invention involves an optical probe, primarily for use in Raman spectroscopy, that can be employed to examine sample sites in vivo. The invention comprises a series of microlenses and microfilters which, in conjunction with an electromagnetic radiation source and a detection system, permit measurement of Raman signals from tissues. Importantly, the probe is small enough to pass inside body cavities such as the vagina, rectum, mouth or a surgically-created cavity. In addition, the probe materials themselves have minimal Raman signature, thereby avoiding Raman "noise" that would interfere with the Raman "signal" generated by the tissue.

The probe employs two optical systems: an excitation leg and a collection leg. The excitation leg delivers electromagnetic radiation to a sample site, while the collection leg collects Raman spectral emissions and delivers them to a detection apparatus. An overview of an exemplary system is show in FIG. 17. The laser light source is directed to a bandpass filter and then to a fiber that carries the electromagnetic radiation. Before reaching the sample, second bandpass filter is employed, and the resulting radiation wavelength is passed through a focusing lens to focus the radiation onto the sample.

Figure 17:
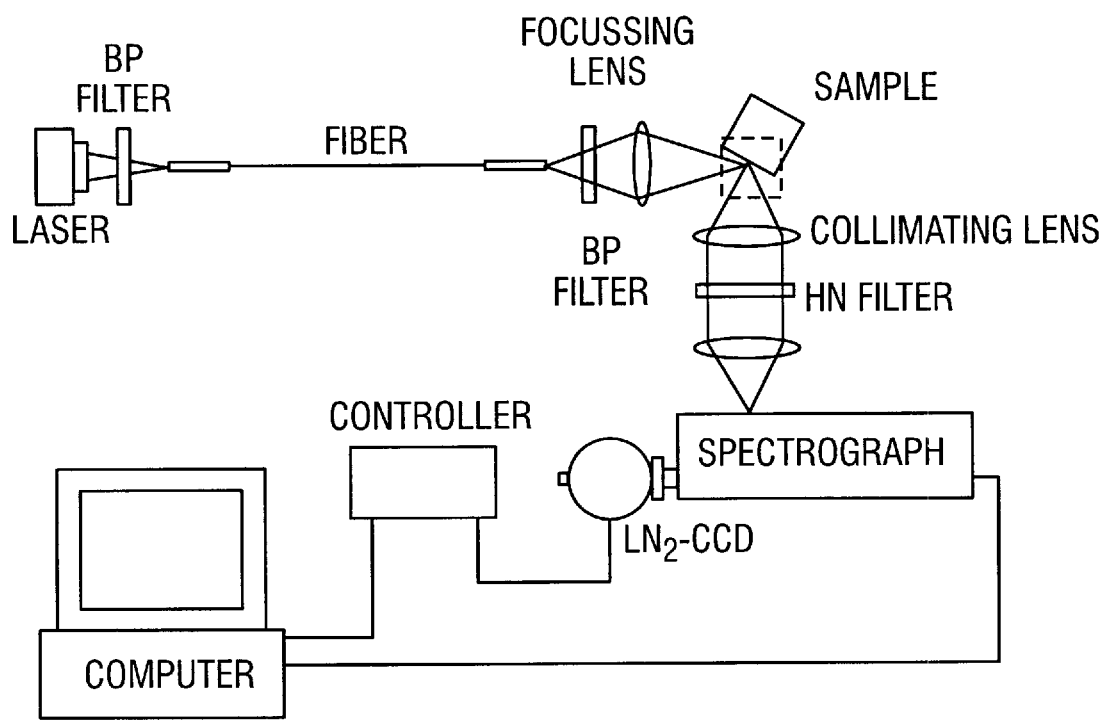
FIG. 17 shows an experimental setup for the collection of near-IR Raman spectra.

Continuing with FIG. 17, the Raman emissions are passed through a collimating lens, a holographic notch filter, and a second focusing lens. Thus processed, the optical emissions are delivered to a spectrograph and photographed with a CCD camera. The data are fed to a computer for further analysis.

The microlenses and microfilters that comprise the probe, along with other probe components, are housed in a probe casing that protects the equipment from the sample, and vice versa. The shape of the probe casing preferably is elongate, generally, to permit its location. Suitable materials for the probe include non-toxic plastics, such as carbonized epoxy, or non-corrosive metals, such as aluminum. More preferably, the probe is a hollow tube. Elements held within the probe may be fixed in place with glues, epoxies or resins. The materials should be kept out of the light pathway.

At one end of the probe, optical conducting materials, such as optical fibers, pass into the probe. This opening should be sealed so that no light can pass into the interior of the probe. Similarly, the optical fibers are covered with light opaque materials, such as black heat-shrink tubing. At the other end of the probe, the opening preferably is covered with a shield to seal the probe interior from the environment while permitting the excitation electromagnetic radiation to pass through, thereby exciting molecules in the sample. The shield also permits Raman spectra from the sample to pass through the shield into the probe for collection purposes. Preferably, the shield material is selected to provide efficient transfer of electromagnetic radiation and reduced Raman interference. Suitable materials include quartz, sapphire and transparent Teflon. Alternatively, a shield may be omitted in its entirety.

For cervical applications, the stiff section of the probe must be at least 13.5 cm, preferably 20 cm, so that it can be advanced through the speculum to the cervix.

The microlenses serve to (i) direct and concentrate the excitation radiation onto the sample area, (ii) expand the emission radiation prior to interference filtering and (iii) concentrate the emission radiation prior to collection. Concentration is accomplished by focusing lenses and expansion is accomplished by collimating lenses. The microfilters serve to (i) eliminate all but the selected wavelength from the excitation beam and (ii) eliminate the excitation wavelength from the emission spectrum. An alternative to filter the excitation wavelength prior to the sample is the use of dielectrically coated fibers that have minimal reflectance. The elimination of the excitation wavelength may be achieved with a holographic notch filter. The combination of these features is particularly effective at achieving the advantages noted above.

Another feature in the probe is the use of a mirror to direct the excitation beam onto the sample site. The mirror uses a polished gold wire; the polishing is conducted so that the beam strikes the normal to the quartz shield at less than the critical angle of quartz to prevent total internal reflection. Optionally, a parabolic mirror may be employed for this purpose.

Figure 12:
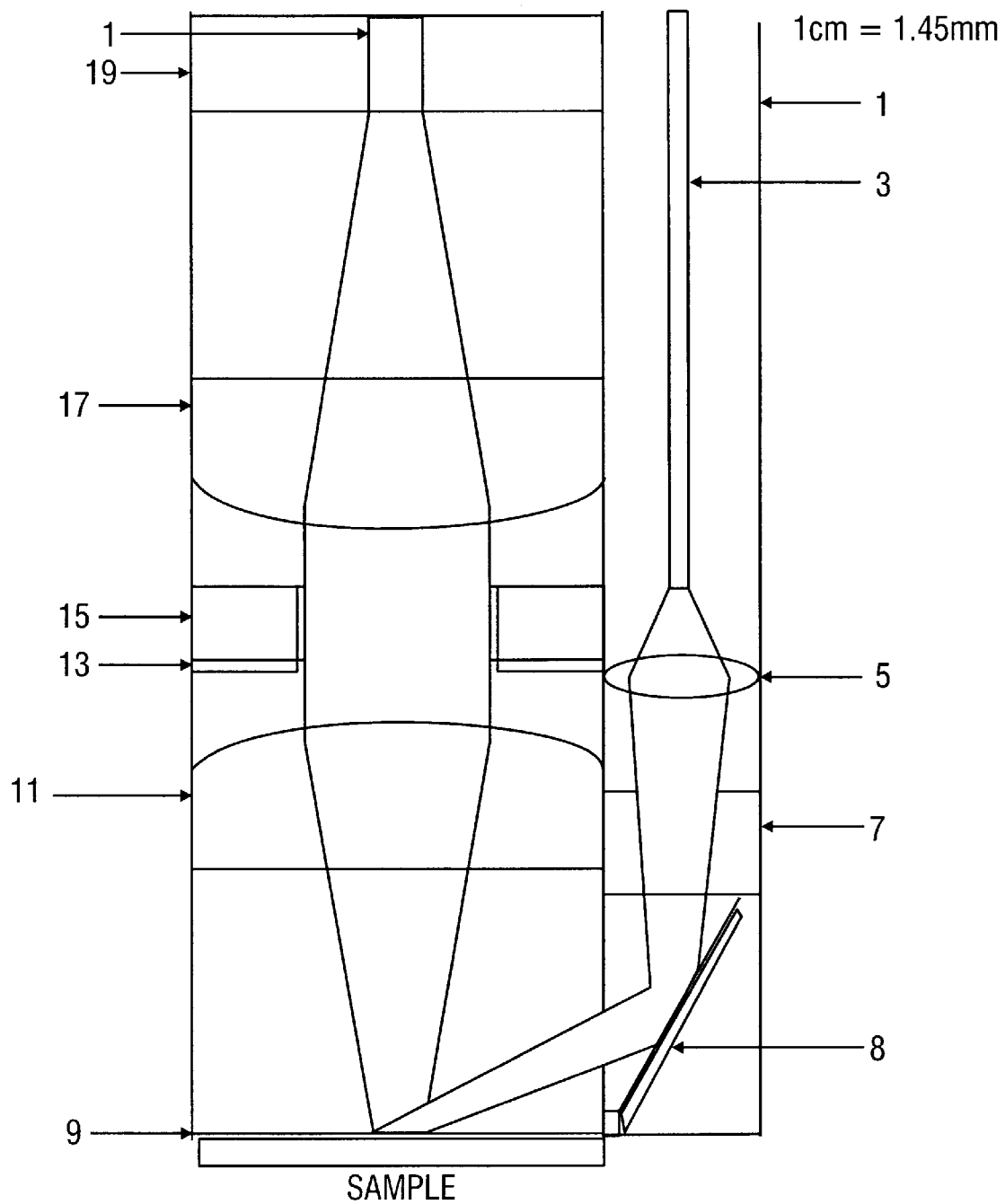
FIG. 12 is a modified schematic (to scale) of the final probe design that was rebuilt to solve the problems observed in the previous iteration. Only the inside face of the probe casing is illustrated. The total length of the probe is about 20 cm, of which only a portion is illustrated.

FIG. 12 shows an exemplary probe configuration. Electromagnetic radiation from the radiation source is delivered to the probe casing 1 and transmitted through a 200 μm core excitation fiber 3. The electromagnetic radiation first passes through a focussing lens 5, and then through a bandpass filter 7. The filtered radiation then strikes a mirror 8 (angle= 67° from normal) and is reflected through the probe window 9 onto the sample area. Emitted radiation passes back through the probe window 9 and through a collimating lens 11 (f=11 mm; d=8 mm). Next the radiation passes through a holographic notch filter 15 (d=8 mm) and then through a second focussing lens 17 (f=11 mm; d=8 mm). An anodized beam stop 13 is located at the notch filter to prevent any extraneous emission from bypassing the filter. The remaining radiation is transmitted out of the probe via fifty 100 μm core diameter collection fibers. The collection fibers are held by a support 19. This radiation is delivered to the detection apparatus. The total length of the probe is 20 cm. The width of the window is 8.5 mm. The total width of the probe is 20 mm.

The dimensions for the exemplary embodiment and the distances between elements can readily be derived from the size bar on FIG. 12. In general, it should be noted that the distance between the sample and the collimating lens should be the focal length of the collimating lens. Similarly, the distance between the collection fibers and the second focussing lens is the focal length of the second focussing lens. In addition, the distance between the first focussing lens and the excitation fiber is such that the image of the excitation fiber is formed at the outer surface of the shield.

The 200 μm core excitation fiber is available as Superguide UV thermocoat 220T from Fiberguide. The first focussing lens is available from CVI Lasers (d=3 mm; f=14 mm). The bandpass filter is available as BP 805-4, Omega. The collimating and second focussing lenses are available from Republic Lenses. The holographic notch filter is available as HIPF-789-8 from Kaiser, Ann Arbor, Mich. The 100 μm core diameter collection fibers are available as Superguide UV thermocoat 120T from Fiberguide. It should be noted, however, that there are suitable, commercially available substitutes for each of the mirror, fibers, filters and lenses described in this paragraph.

Lasers generally are employed as the electromagnetic radiation source. In accordance with the present invention. For example, a 40 mW GaAlAs diode laser (Diolite 800, LiCONix, Santa Clara, Calif.) can be used to excite samples at 789 nm through a 100–200 μm core diameter glass optical fiber. Laser power may advantageously be maintained at 15 mW (±1%).

An exemplary detection system includes an imaging spectrograph (Holospec f 1.8, Kaiser, Ann Arbor, Mich.) and a liquid nitrogen cooled CCD camera (LNCCD-1024 EHRB, Princeton Instruments, Trenton, N.J.). The spectrograph may advantageously be used with a 300gr/mm grating, blazed at 500 nm, which yields a spectral resolution of 10 $cm^{-1}$ with an entrance slit of 100 μm. Alternatively, one may employ a series of bandpass filters and avalanche photodiodes to detect selected emission frequencies. A computer (Austin 486 75 Mhz, Austin, Tex.) is used for data processing.

II. In Vivo Methods

One use to which the probe of FIG. 12 may be applied involves the detection of tissue abnormality in a tissue sample. Four basic steps are involved: (i) providing a tissue sample; (ii) illuminating said sample with an electromagnetic radiation wavelength from the near infrared to produce a Raman spectrum shifted from the illumination wavelength; (iii) detecting a plurality of emission frequencies of said spectrum; and (iv) establishing from said emission frequencies a probability that said sample is abnormal. The illumination wavelength may be about 700–850 nm, and more specifically about 790 (+/−10) μm.

The establishing step may comprise measuring said emission frequencies relative to the illuminating electromagnetic radiation wavelength. Relevant emission frequencies are advantageously shifted about 626, 818, 978, 1070, 1175, 1246, 1330, 1454 and 1656 $cm^{-1}$ from an illumination wavelength of 789 nm. For example, emission frequencies shifted about 1070 $cm^{-1}$ and about 1656 $cm^{-1}$ from the illumination wavelength distinguish precancers and non-precancers. Emission frequencies shifted about 1330 and 1656 $cm^{-1}$ from the illumination wavelength distinguish precancer and non-precancers. Emission frequencies shifted about 1454 and 1656 $cm^{-1}$ from the illumination wavelength distinguish low grade precancerous and high grade precancerous.

Part of this method relies on a mathematical model for predicting abnormality in a tissue sample. This model is derived from a statistical analysis of samples and involves forming a set of principal components from preprocessed data, the principal components being defined as providing statistically significant differences between normal tissue and various forms of abnormal tissue. Further, the principal components are subjected to logistic discrimination to develop the relevant mathematical model.

In another embodiment, the method of detecting tissue abnormality in a tissue sample focuses on determining the Raman signatures of particular molecules, for example, collagen, phospholipids and glucose-1-phosphate. This method is fully described in a U.S. patent application, filed on Jun. 19, 1996, entitled "NEAR-INFRARED RAMAN SPECTROSCOPY FOR IN VITRO AND IN VIVO DETECTION OF CERVICAL PRECANCERS," which is incorporated herein by reference in its entirety.

In a clinical setting, the Raman spectroscopy system of the present invention is applied as follows:

The instrument should be turned on and calibrated for spectral responsivity and intensity.

Acetic acid is applied to the cervix. Areas to be inspected are identified.

The probe is directed to each area on the cervix to be inspected. Multiple placements of the probe may be necessary. Use of a visible guiding beam will ensure that the active area of the probe is aligned with the intended area of the sample. One of the optical fibers in the collecting leg may be coupled to a laser and used to provide the visible guiding beam.

The cervix is illuminated with excitation wavelengths at about 789 nm. The probe will detect the resulting spectrum, which will contain a combination of tissue fluorescence and Raman signals.

Data from each spatial location assessed will be processed to remove the fluorescence information, improve the signal to noise ratio, resulting in the Raman spectrum from each site. Analysis steps carried out in the instrument software include:

Data recorded from each spatial location on the cervix are pre-processed in two ways, fluorescence subtraction and convolution.

Fluorescence subtraction is carried out by fitting the tissue spectrum to a low order (3rd–5th) polynomial, which captures the slowly, spectrally-varying fluorescence information, but not the narrow band Raman information. The best fit polynomial is then subtracted from the tissue spectrum, yielding the Raman spectrum.

The resulting Raman spectrum is then convolved with a Gaussian function whose width matches the spectral resolution of the spectrometer. This improves the signal to noise ratio of the Raman spectrum.

The processed data vector from each site (DN') is then used to determine the condition of the measured tissue. This can be accomplished in several ways. In one method, the processed data vector is multiplied by the reduced eigenvector matrix stored in memory (Cn'). Cn' contains only those eigenvectors which displayed statistically significant differences for sample to be classified.

The Fisher score is calculated for each sample using Fisher's discriminant analysis. In this calculation, the mean values and standard deviations of the PC scores for normal squamous epithelium and SILs stored in memory are used.

Using this algorithm, sites with a Fisher score of being normal squamous epithelium greater than a threshold value Raman signal generated by rhodamine 6G was back-calculated, given that 6.4 electrons/second were detected by the CCD camera. In this calculation, the detached signal was divided by the fractional signal lost at each signal interface in the system to obtain the amount of Raman signal collected by the collimating lens in the in vitro setup. Table 1 shows these SIN calculations for each step along with the equations used. A Lambertian distribution (29) was used to calculate the Raman signal generated by rhodamine 6G for a given spot size which accounts for the angular distribution of Raman scattering.

Figure 1:
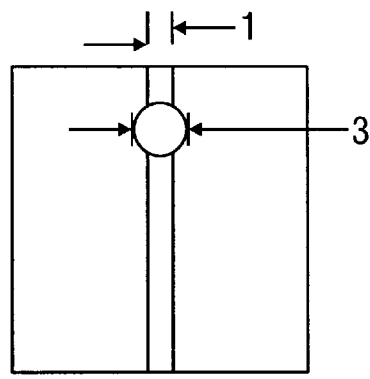
FIG. 1 is an illustration of the overlap in the imaging beam at the entrance slit of the spectrograph. (1) 100 mm slit; (3) 200 mm imaging spot.

Table 1 shows that 93% of the light was lost at the imaging end due to mismatch in the numerical aperture (NA) between the collection lenses (which performed 1:1 imaging) and the spectrograph. The mismatch in spot to slit size at the entrance of the spectrograph accounted for an additional 37% loss. Note that a 100 $\mu$m slit was used at the entrance of the spectrograph with the spot size at the sample at 200 $\mu$m in the in vitro system (FIG. 1).

TABLE 1

Signal-to-noise calculation showing the light losses in the path of collection for different configurations.

Figure 8:
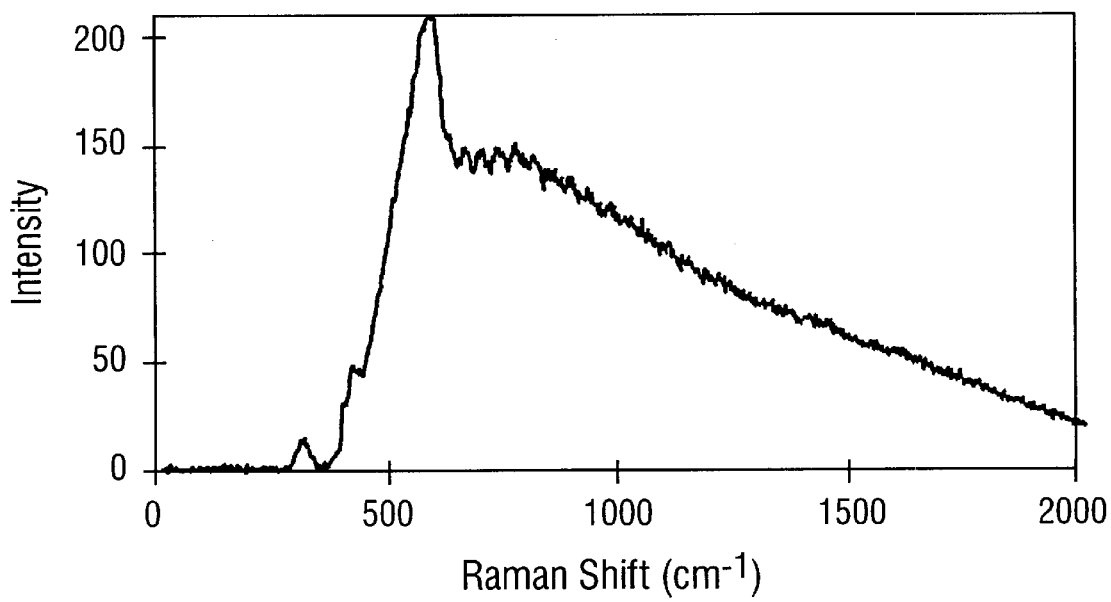
FIG. 8 shows a Raman spectrum of the collection leg of the probe in FIG. 6.

| Variables | Relationship | in vitro units setup | 50(100 $\mu$m) fibers (Initial Probe) | Probe | Probe (QE) | Probe (QE & Power) |
|---|---|---|---|---|---|---|
| Time Integration | for tissue | 900 sec | 21 | 370 | 80 | 1 |
| Improvement Factor | $S_{new}S_{old}$ | | 42.5 | 2.4 | 11.3 | 24.8 |
| Detected Signal of rhodamine 6G | divide by time | 6.4 e/sec | 272.04 | 15.51 | 72.37 | 385.9 |
| loss factor | product of all losses | 0.0342 | 2.044 | 1.23 | 5.72 | 30.53 |
| CCD quantum efficiency | at 1656 cm$^{-1}$ (900 nm) | 0.15 | 0.15 | 0.15 | 0.7 | 0.7 |
| Transmittance of grating | estimated | 0.8 | 0.8 | 0.8 | 0.8 | 0.8 |
| Reflectance of mirrors | estimated | 0.997 | 0.997 | 0.997 | 0.997 | 0.997 |
| Area mismatch at slit | lit area/image area [FIG. 8.1] | 0.636 | 1 | 1 | 1 | 1 |
| NA mismatch | $\tan^2(a*SIN(NA_{spec}))/\tan^2(a*SIN(NA_{coll}))$ | 0.026 | 0.99 | 0.99 | 0.99 | 0.99 |
| Transmittance of glass | estimated | 0.9801 | 0.98 | 0.98 | 0.98 | 0.98 |
| Fresnel Losses | estimated | 0.78 | 0.78 | 0.78 | 0.78 | 0.78 |
| Transmittance of filter | estimated | 0.9 | 0.9 | 0.9 | 0.9 | 0.9 |
| Power | measured | 25 mW | 25 | 15 | 15 | 80 |
| Raman signal collected | total signal/Lfactor | 187.25 ph/sec/mW | 133.08 | 12.644 | 12.644 | 12.644 |
| Area of collection | pi*r$^2$ - radius of fiber or lens | 5.067 cm$^2$ | 0.00785 | 0.00785 | 0.00785 | 0.00785 |
| Distance to sample | D | 3.3 cm | 0.1 | 0.9 | 0.9 | 0.9 |
| Angle of collection | from sample normal to fiber | 75 degrees | 7.83 | 33 | 33 | 33 |
| Lambertian factor | D$^2$/(COS(angle)*pi*$^2$) | 8.304 l/sr | 128.52 | 122.97 | 122.97 | 122.97 |
| Total signal generated | product of Lfactor and signal | 1554.89 ph/sec/sr/mW | 1554.89 | 1554.89 | 1554.89 | 1554.89 | stored in memory are classified as non-SIL. Remaining sites are classified as SIL.

Other methods of analysis would include using intensites at 1070 cm$^{-1}$ and 1656 cm$^{-1}$ to determine whether a sample is precancerous, using intensities at 1330 cm$^{-1}$ and 1656 cm$^{-1}$ to determine whether a sample is precancerous, and using intensities at 1454 cm$^{-1}$ and 1656 cm$^{-1}$ to determine if a precancer is low grade or high grade.

III. In Vitro Raman System

Figure 2:
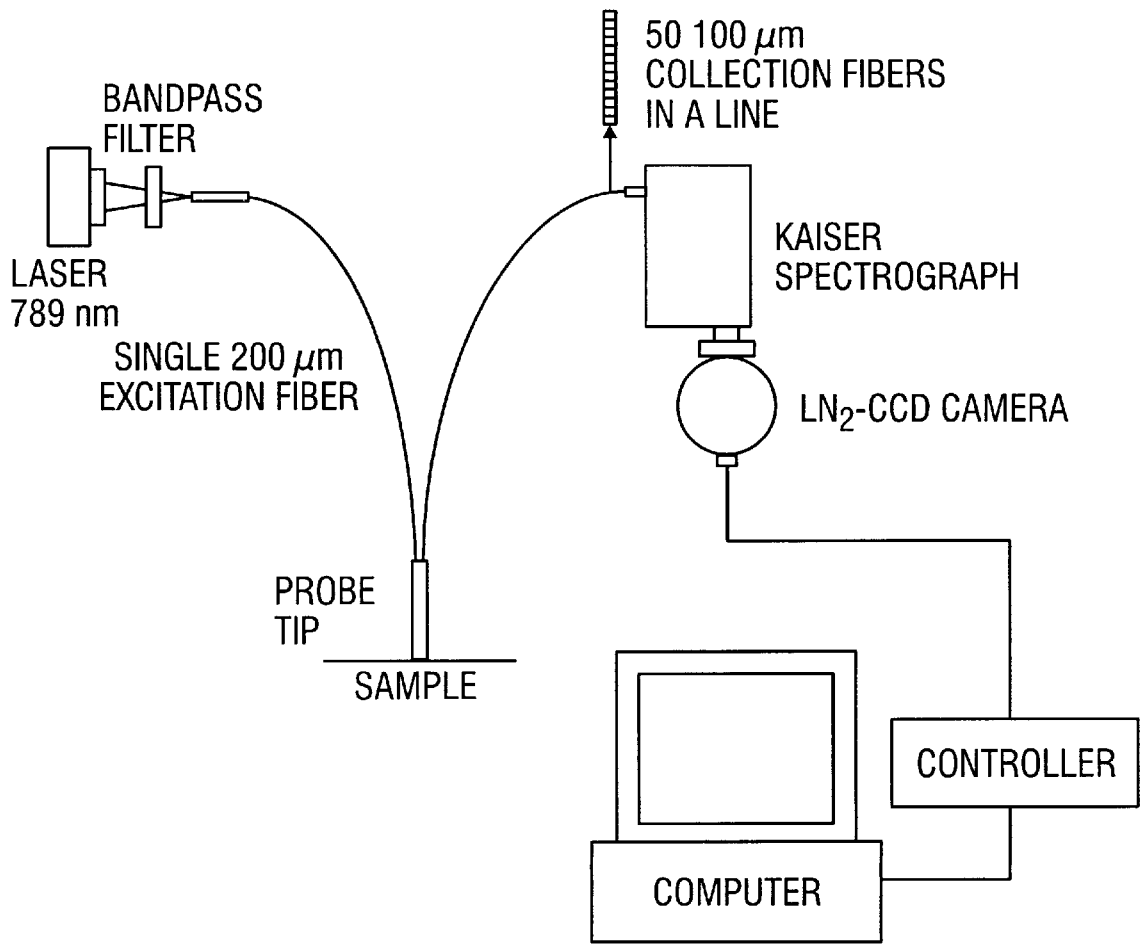
FIG. 2 is a schematic of the basic clinical Raman system.

To obtain tissue Raman signal with acceptable signal to noise ratio (S/N), the signal from cervical biopsies has been integrated for about 15 minutes using an earlier in vitro Raman system. To construct a feasible clinical system, the integration time needs to be significantly reduced to the order of a few minutes. In order to determine the sources of loss in the in vitro system, signal to noise calculations were performed at every step of the light path. The amount of To account for the NA mismatch, a new spectrograph (Kaiser Holospec, Ann Arbor, Mich.) with an NA of 0.27 (comparable to that of a typical fiber) was used in the clinical Raman system. To maintain the spectral resolution of the system at 10 cm$^{-1}$, a 100 $\mu$m slit needs to be used in the clinical system as well. Hence, 100 $\mu$m core fibers were selected for the probe collection bundle to minimize signal loss due to this mismatch. The power of the excitation light could be potentially increased to further improve the S/N and hence reduce the integration time. However, in consideration of the ANSI safety standards, a higher power laser was decided against at that time. FIG. 2 shows the clinical Raman system developed as described above where the same basic system except the probe used is maintained throughout these studies.

IV. In Vivo Probe Development

Based on the S/N calculations, all in vivo probes were designed to have a single excitation fiber with a 200 $\mu$m core diameter. Multiple 100 $\mu$m core collection fibers were used.

The collection fibers were aligned to form a line of fibers at the spectrograph. The height of CCD camera determines the number of fibers that can be imaged by the detector. The height of the CCD camera used in the Raman system is 6.7 mm and hence a maximum of 50 collection fibers could be used.

Initial Probe Design: The first fiber optic probe was designed to collect Raman spectra prior to knowledge of fiber signal interference. This probe consisted of a central excitation fiber (200 $\mu$m core diameter) surrounded by 50 collection fibers (100 $\mu$m core diameter) at the probe tip. The excitation fiber was coupled to the laser and the collection fibers were linearly aligned at the entrance slit of the spectrograph. The probe was tested with and without a quartz shield (1 mm thick) at the probe tip. Table 1 also shows S/N calculations performed to estimate the improvement in Raman signal collection when fifty 100 $\mu$m collection fibers, with 0.22 NA, are used. The power and spot size of illumination and collection used in the in vitro studies were retained. The matching in NA as well as the spot size at the entrance slit of the spectrograph were included. All other parameters were maintained as before. An improvement factor of 43 was obtained thus reducing the integration time to 20 seconds for a S/N similar to in vitro Raman spectra (Table 1, column 5). However, tissue signal could not be detected using this probe.

Subsequent Probe Designs: The interfering fiber signal is generated in the delivery fiber by the excitation light. In addition, signal also is generated in the collection fibers by the elastically scattered light as well as the Fresnel reflected excitation light returning into the collection fiber(s). A feasible probe design should prevent unwanted signal generated in the delivery fiber from illuminating the sample as well as prevent elastically scattered excitation light from entering the collection fibers and generating unwanted signal. A bandpass filter could be placed after the excitation fiber allowing only the transmission of the excitation light and blocking the Raman signal from the delivery fiber. A long pass filter which blocks the transmission of the Fresnel reflected excitation light, as well as the elastically scattered light, from entering the collection fibers filter could be placed between the sample and collection fibers, preventing the generation of fiber signal from the probe.

Figure 3:
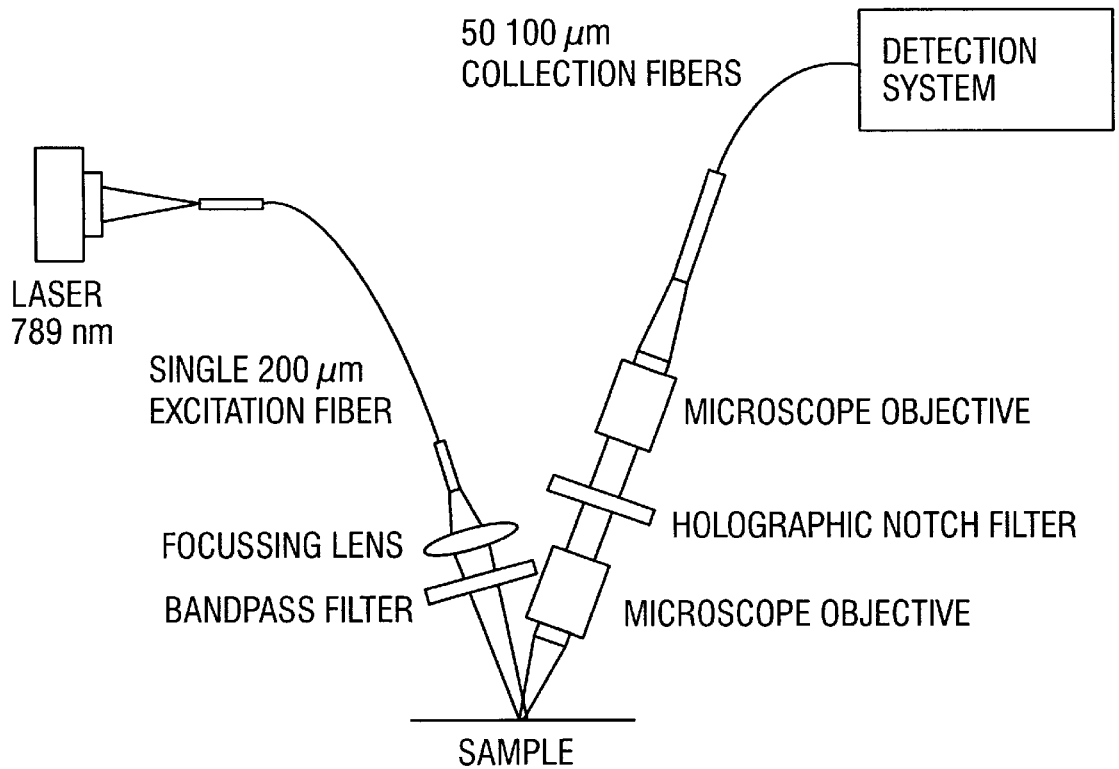
FIG. 3 is a schematic of a table top setup to test the source of fiber signal.

Naphthalene (which is highly elastically scattering) was used as a standard to ascertain the primary source of the fiber signal observed. A table top experimental setup was arranged to perform these tests (FIG. 3). The separate excitation and collection legs were placed at a small angle relative to each other. The excitation beam was focused on the sample. The collected Raman scattering was collimated and then refused onto the imaging bundle of fibers (fifty 100 $\mu$m collection fibers).

Figure 4A:
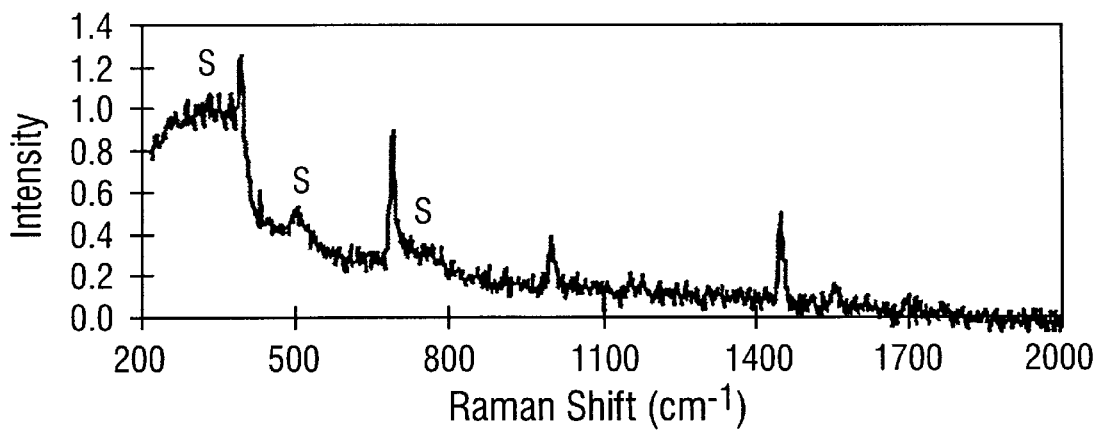
FIGS. 4A–D show Raman spectra of naphthalene with (FIG. 4A) no filters, (FIG. 4B) only a bandpass filter, (FIG. 4C) only a holographic notch filter and (FIG. 4D) both bandpass and notch filters between the sample and fibers. [S] indicates silica bands, [N] indicates naphthalene bands.
Figure 4B:
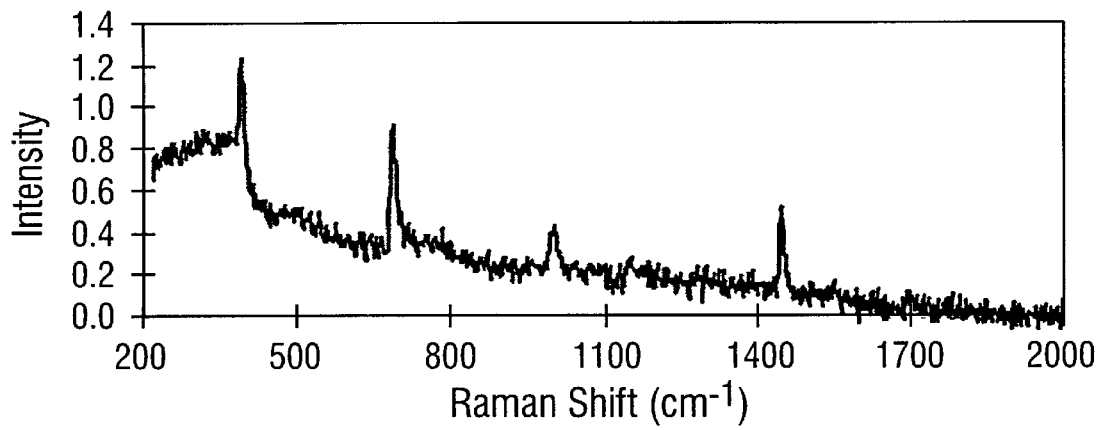
Figure 4C:
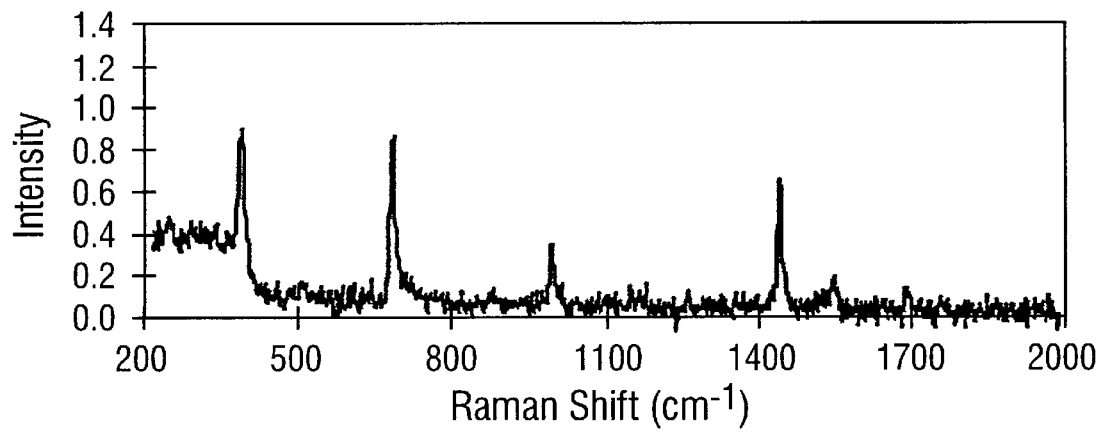
Figure 4D:
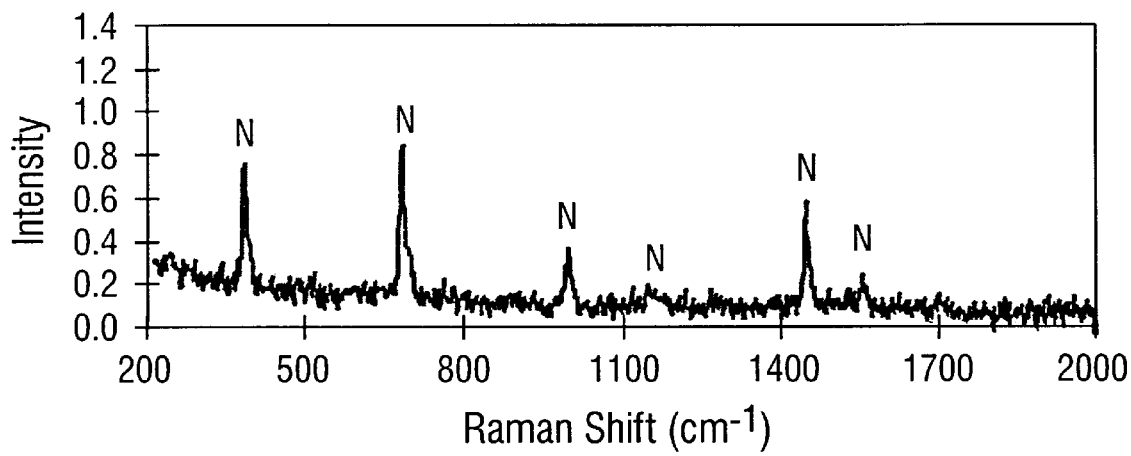

FIG. 4A–D shows the Raman spectra of naphthalene obtained with (A) no filters between the sample and the fibers, (B) only a bandpass filter between the sample and excitation fiber, (C) only a holographic notch filter between the sample and collection fibers and (D) both bandpass and notch filters between the sample and fibers. A significant silica Raman signal is detected in FIG. 4A–C, indicating that significant proportions of silica signal are generated in the excitation and collection fibers. FIG. 4D shows that filters are needed to block the fiber interference from both the excitation and collection fibers of the probe.

Detectable tissue Raman signal could be obtained using the table top setup with 5 minute integration time. The next sections described several configurations of a fiber optic probe that were designed to reduce these fiber effects. It should be noted that the fiber probe is being designed to use on the human cervix and hence needs to be compact in configuration while collecting maximum tissue Raman signal.

Preliminary Design of Clinical Probe: The simplest design would require the face of the fibers in the probe to be coated with appropriate dielectric materials that accomplish the filtering of excitation electromagnetic radiation. It is possible to obtain optical fibers with anti-reflective coating at its tip. Using this approach, it is possible to coat the excitation fiber such that it only transmits the excitation light at 790 $\mu$m (+/−10 nm) and blocks the longer wavelengths. It also is possible to coat the collection fibers such that light at 790 $\mu$m is blocked while transmitting longer wavelengths. It was found that although this is feasible, it is extremely expensive. Moreover, the rise band of transmission of the coatings may be more gradual than acceptable for Raman measurements (a rise band of 25 nm is required while both coatings would have a 60 nm rise band to transmit or block only above 850 nm). A longpass or notch filter with bandpass characteristics at its center could be placed at the tip of the fiber bundle to provide the same filtering effect as would coatings.

Figure 5A:
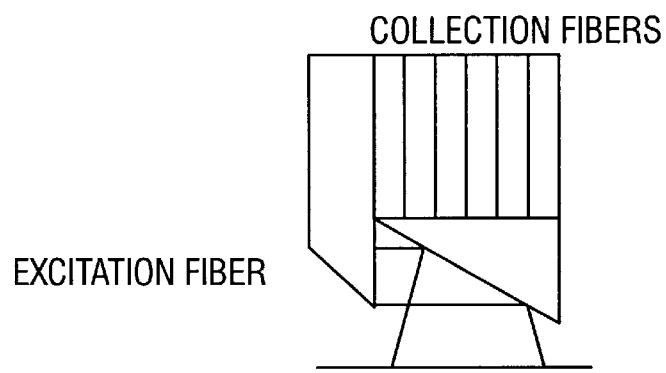
FIGS. 5A–B are schematics of Raman probe designs using a dichroic mirror to filter the fiber interference using a wedged coated as a dichroic (FIG. 5A) or a flat dichroic placed at an angle (FIG. 5B).
Figure 5B:
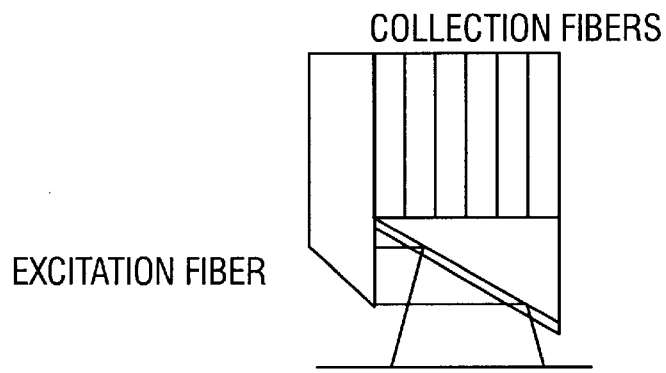

FIG. 5 illustrates another design that could be easily implemented as a Raman probe. A dichroic mirror that reflects the excitation light at 790 nm and transmits light at longer wavelengths, could be used at the probe tip to provide the filtering required to block fiber interference. This mirror may be optically flat that is placed at a 45° angle or a wedge with a dichroic coating. This probe consists of a side firing excitation fiber at 790 nm which is reflected by the dichroic mirror.

The Raman signal at longer wavelengths is transmitted by the mirror on to the 50 collection fibers packed together. A dichroic mirror as small as 3 mm is available commercially. Hence, it is feasible to build such a probe. Presently, optimal dichroic mirrors are usually only about 90% efficient, however, which may not provide sufficient blocking, in and of itself, of the excitation fiber Raman or the excitation light into the collection fibers.

Figure 6:
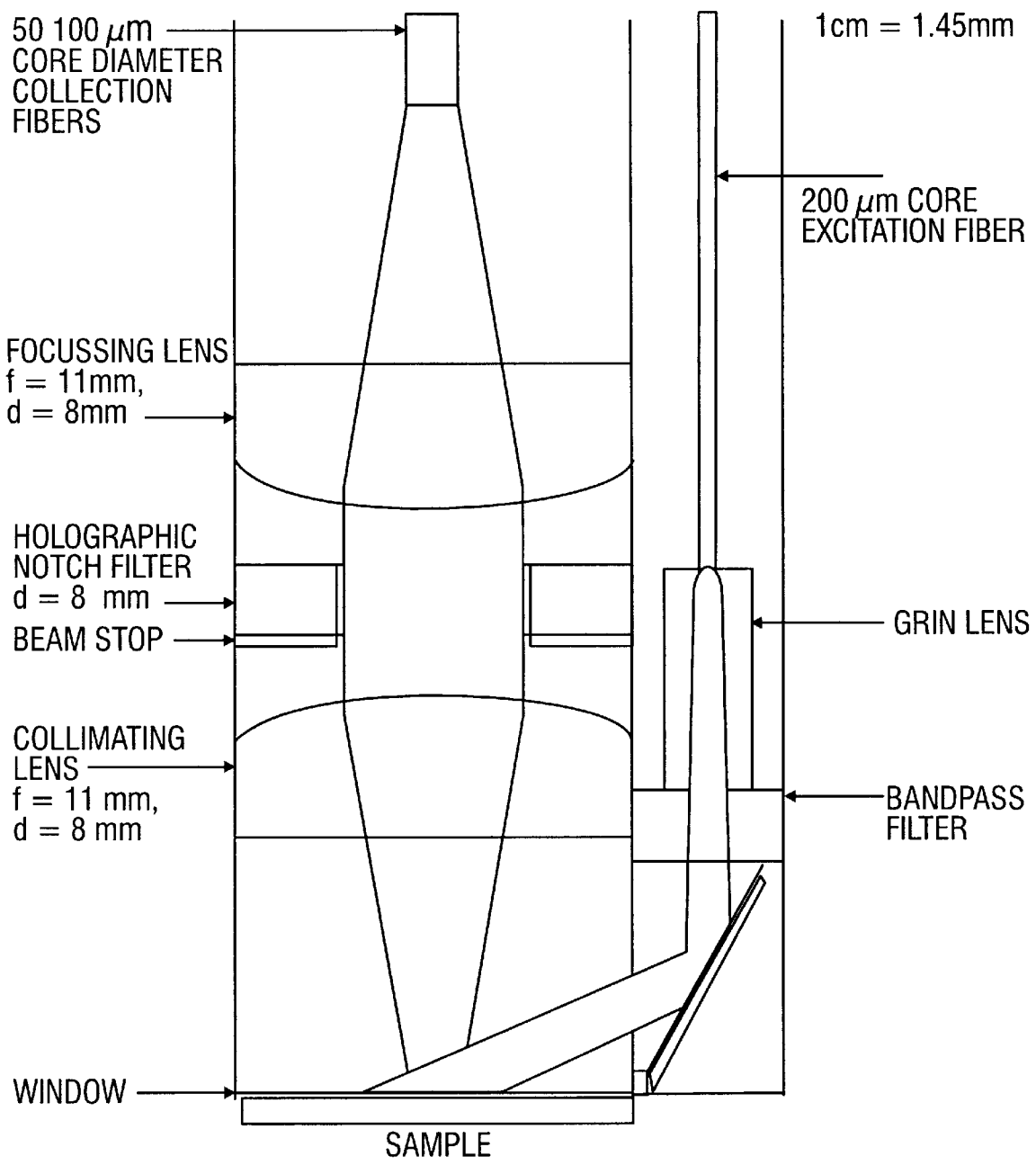
FIG. 6 is a schematic (to scale) of the final probe design selected to be implemented as a clinical Raman probe. The probe was first built using this design. Only the inside face of the probe casing is illustrated.

Penultimate Probe Design: FIG. 6 shows a transverse section of the probe design that was chosen to be implemented as a Raman probe. This probe design is based on the optrode by Myrick et al. (30) and represents a miniaturization of the table top setup described in FIG. 3 with further improvements for the in vivo application. Rather than placing the excitation leg at an angle, a mirror is placed in the excitation path to deflect the beam onto the sample. This probe was designed using the smallest available physical dimensions of both the bandpass and holographic notch filters. However, filters are, in general, most efficient when light is normally incident, hence the excitation and collection legs were initially designed to collimate the light in the probe. This requirement is more rigid for the holographic notch filter. The excitation light is delivered by a 200 $\mu$m core fiber coupled to a 0.18P graded-index (GRIN) lens which approximately collimates the beam. A 3 mm round bandpass filter was placed after the GRIN lens to transmit the excitation light and block the longer wavelengths. This deflecting mirror in the excitation leg of the probe can be a flat mirror that does not affect the excitation beam. A parabolic mirror also can be used such that the beam is focused onto the sample increasing the incident irradiance. The requirements for a parabolic mirror are very specific in dimensions as well as in its focal length. Due to the unavailability of an appropriate parabolic mirror, a flat mirror was used. A gold wire was polished at an angle of 67° from the normal and glued in place such that the deflected excitation and normal collection spots overlap.

The Raman signal from the sample is collected by the first lens and collimated. An 8 mm round holographic notch filter blocks the excitation light with an OD of 6 and transmits at the longer wavelengths with an efficiency of 90%. A second lens focuses the beam onto the 50 tightly packed collection fibers. Although the external diameter of the notch filter is 8 mm, the working area of the filter is only 4 mm in diameter. Hence the lenses were designed to yield a collimated beam that is less thin 4 mm in diameter while producing a 1:1 image at the collection fibers. These fibers are arranged in a line at the detection end. One of the collection fibers was directed to form an additional leg to couple a helium neon laser through it, to provide an aiming beam during the placement of the probe on the sample. A quartz shield was used at the tip of the common end of the probe forming a barrier between the probe optics and the sample. Quartz was selected as the material of choice as its fluorescence and Raman signal were known and any additional background signal from the probe could be identified.

Figure 7:
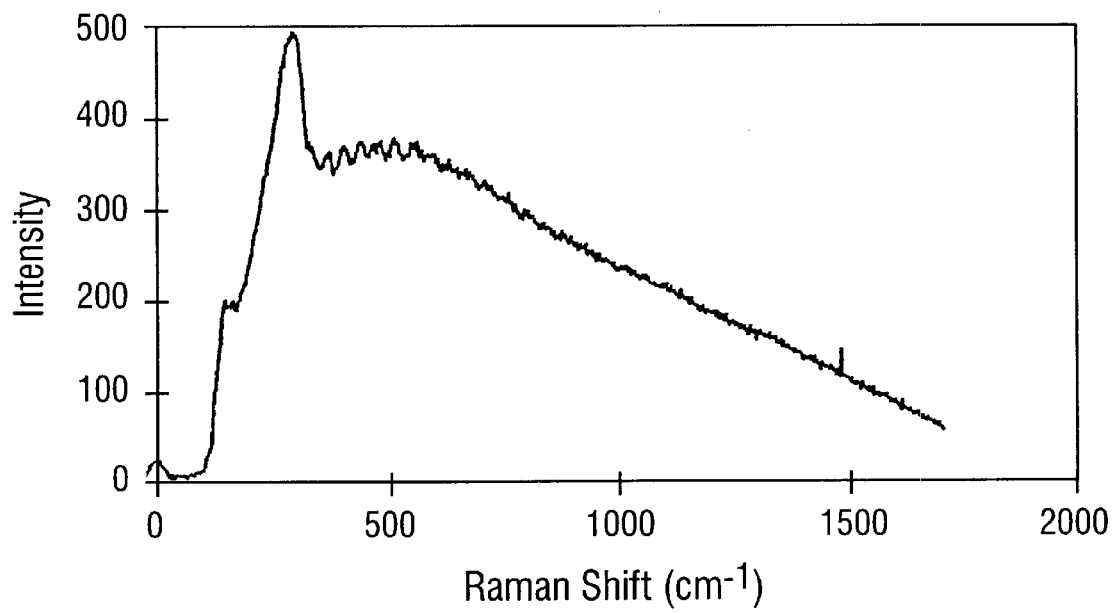
FIG. 7 shows a Raman spectrum measured with the probe illustrated in FIG. 6 in air, 1 minute integration.

The first iteration of the probe, shown in FIG. 6, could not be used to measure tissue Raman spectra. FIG. 7 shows the background subtracted spectrum obtained for 1 minute integration using the system in FIG. 2 and the probe in FIG. 6 held in air. A large fluorescence signal is observed, in addition to some silica Raman signal. Tests were performed to identify the source of the problem.

Figure 9:
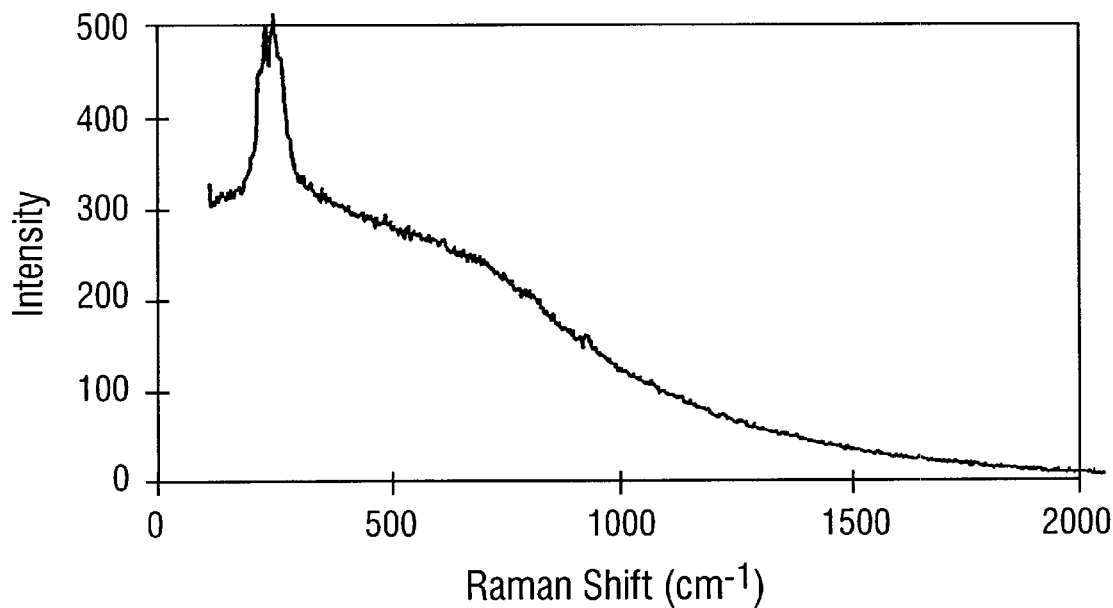
FIG. 9 shows a Raman spectrum of the excitation leg of the probe in FIG. 6.
Figure 10:
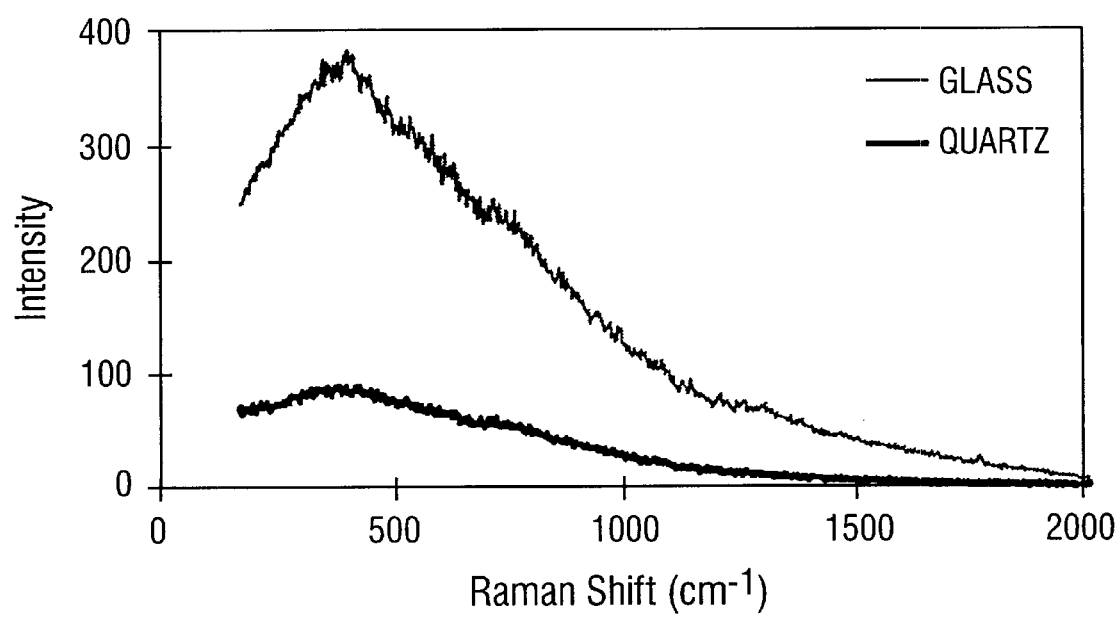
FIG. 10 shows spectra of quartz and glass to indicate the advantage of using quartz instead of glass.
Figure 11:
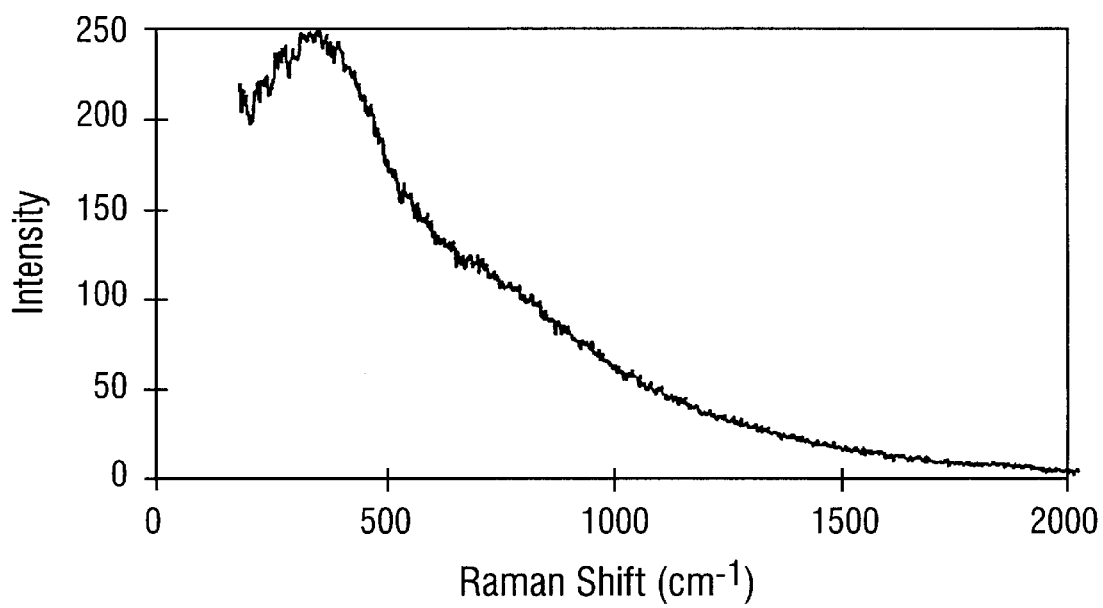
FIG. 11 shows a spectrum obtained from the bandpass filter used in the probe (FIG. 6) using the in vitro Raman system.

Excitation light was directed into the collection end of the probe and the resultant signal was measured by the detector (FIG. 8). FIG. 9 shows the signal detected when the light from the excitation leg of the probe is directly coupled into the spectrograph. FIGS. 8 and 9 show that fluorescence is generated in both legs of the probe. It was identified that glass lenses had been used in the collection leg which have a greater signal than quartz. The excitation spot at the sample was 2.3 mm in diameter, while only a 1 mm spot was imaged by the collection fibers. Due to the large excitation spot size, the mirror used to direct the beam onto the sample was being overfilled resulting in multiple reflections of light as well as signal from the glue which holds the mirror in place.

In addition, the bandpass filter also shows a significant fluorescence signal (11,31). The bandpass filter was determined to be made of absorption glass which generates fluorescence. When the probe is placed on a tissue sample, only the fluorescence signal is detected from the probe. This inherent probe fluorescence results in a proportional shot noise which obscures any tissue Raman signal present. It was necessary to eliminate a significant amount of this background fluorescence before any tissue Raman signal can be detected.

A new probe, which is the probe of FIG. 12, was constructed using the same basic design described in FIG. 6 with several modifications. First, the glass lenses in the collection leg were replaced with quartz lenses. Second, the excitation beam was focused such that the excitation and collection spots overlapped. Hence, the GRIN lens in the excitation leg was replaced with a 3 mm diameter quartz lens to yield a 900 $\mu$m excitation spot. The excitation beam was verified to be incident within the dimensions of the mirror. Third, the inner surfaces of the metal tubings used to house the probe optics were anodized to reduce the incidence of multiple reflections of light. Fourth, a new bandpass filter without absorption glass was used. Fifth, the existing quartz shield was replaced with a thinner one (0.5 mm instead of 1 mm). Although the use of an anti-reflective coated quartz shield was considered, it was not implemented due to potential Raman or fluorescence signals generated by the coating.

Figure 13:
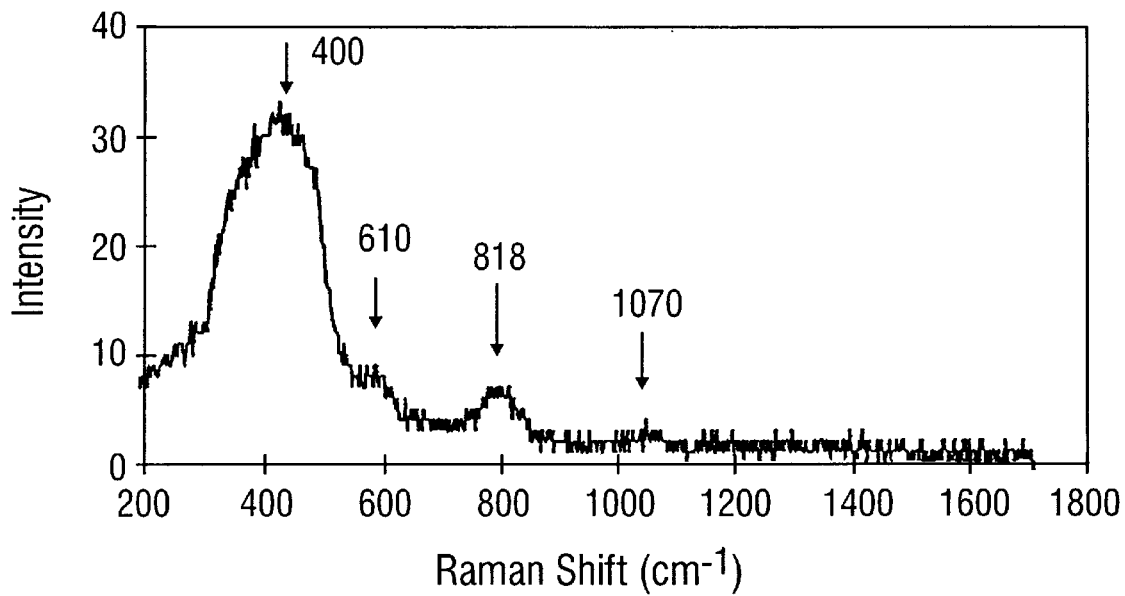
FIG. 13 shows a background spectrum measured with the reiterated probe in FIG. 12 in air (1 min. integration).

FIG. 13 shows the signal obtained with the reiterated probe of FIG. 12 in air for 1 minute integration. Unlike the spectrum in FIG. 7, no fluorescence is observed. The peaks observed at 400, 626 and 818 $cm^{-1}$ are silica Raman peaks which arise from the quartz shield used as expected. The efficiency of this detection system results in a calculated reduction in time integration to about 80 seconds (Table 1, column 6).

Figure 19:
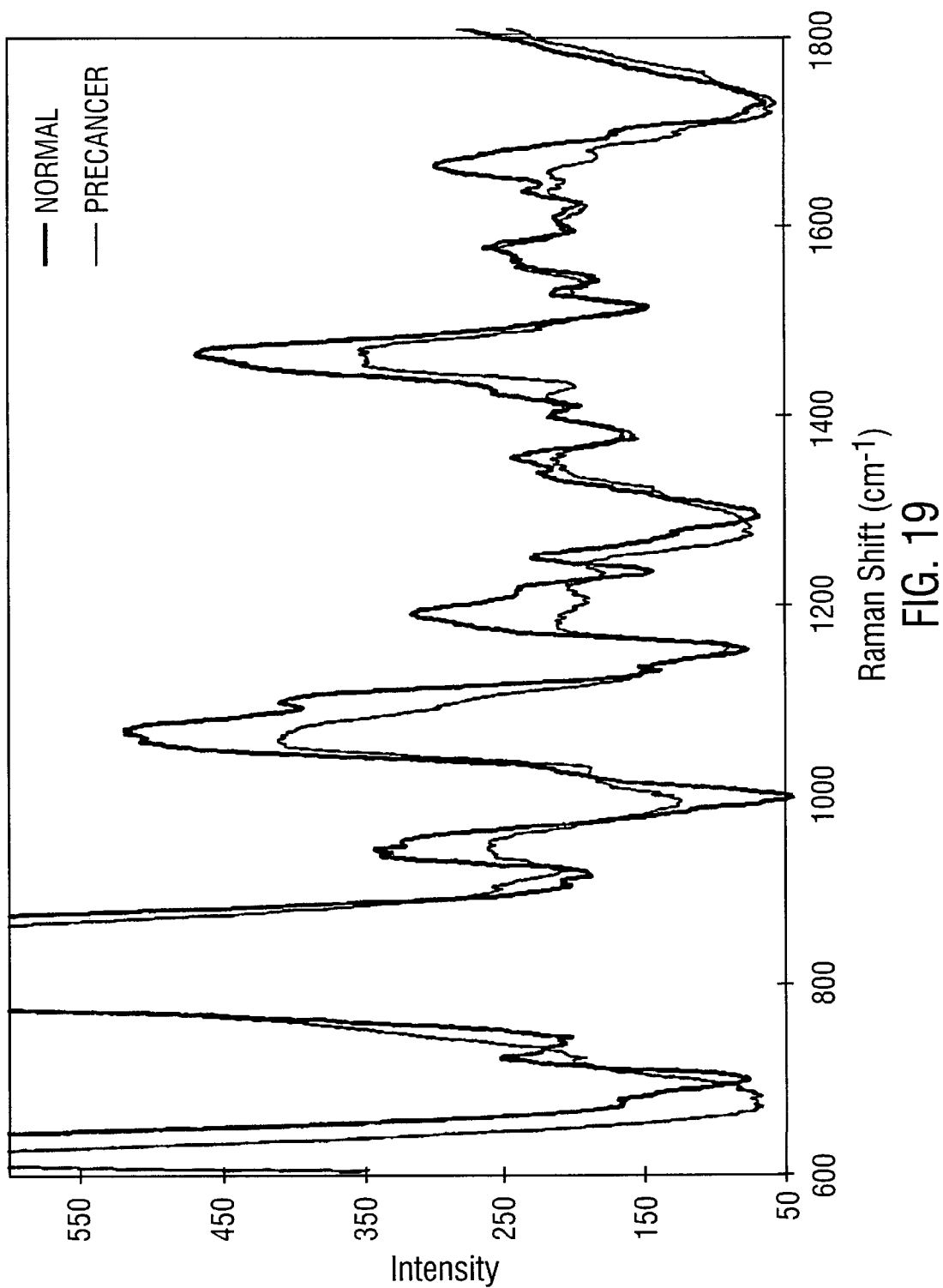
FIG. 19 shows in vivo Raman spectra from one normal and one precancerous site in one patient measured using a deep depletion CCD camera.

A CCD camera was tested using the Raman probe of FIG. 12 and system described in FIG. 17. Raman spectra were acquired in vivo from three patients using this CCD camera with two minute integration time. FIG. 19 shows the spectra obtained from a normal versus precancerous lesion from one of these patients. A back-illuminated chip is known to produce etaloning as a result of multiple reflections of the photons within the chip, which is observed as an interference pattern overriding the measured spectrum detected by the camera. However, it is observed that the test camera displays only a 3–4% etaloning which is not manifested in the observed Raman spectrum (FIG. 19).

The tissue Raman spectra were analyzed only between 600 and 1800 $cm^{-1}$; the silica peak at 400 $cm^{-1}$ is not considered relevant for tissue Raman acquisition. The probe was tested on the buccal mucosa of a volunteer and Raman signal with S/N slightly lower than that of in vitro tissue Raman spectra was obtained. Five minutes time integration was required. This corresponds with the results displayed in Table 1, column 6, which calculates a time integration of 370 seconds (~6 min).

V. Examples

The following examples are included to demonstrate preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods: Background interference from a probe was tested using Raman signals obtained from rhodamine 6G, naphthalene, potassium iodide and in air and compared to that obtained using the in vitro system shown in FIG. 17 with the bandpass filter placed after the excitation fiber. Spectra acquired from cervical biopsies in vitro and from mouth in vivo were used to test the efficiency of the system for obtaining tissue Raman spectra.

NIR Raman spectra of the cervix were successfully measured in vivo from 4 patients. Each patient underwent a complete exam which included a history, a Pap smear and colposcopy of the cervix, vagina and vulva. In all except one patient, spectra were acquired from about two sites in each patient after colposcopic examination of the cervix. Biopsies were obtained only from abnormal sites analyzed by the probe and histology was performed.

In vivo Raman spectra from the cervix were obtained using the same laser and detector as in FIG. 17. The new spectrograph and probe (FIG. 12) were used. The laser power at the tip of the probe was 15 mW with a spot size of 900 $\mu$m. All in vivo spectra were obtained with 5 minute time integration. The tissue Raman spectra were background subtracted and calibrated for the wavelength dependence of the filters, spectrograph, grating and detector. The calibrated Raman spectra were then noise-smoothed using a Fourier filter as well as fluorescence-subtracted using a high order polynomial fit (22).

Results: NIR Raman spectra of the cervix were measured in vivo from four patients. Of the four patients studied, one patient (Patient 2) had an abnormal lesion which was biopsied. The biopsy was histologically classified as a high grade squamous intraepithelial lesion (SIL) with moderate severity. All others were follow-up patients with a normal cervix.

Figure 14:
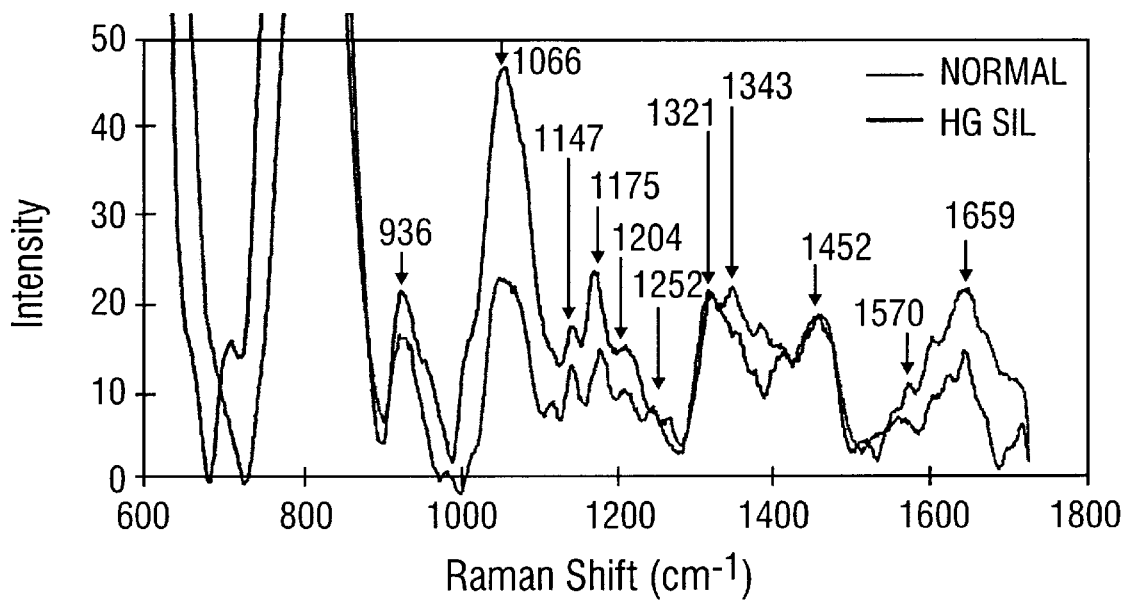
FIG. 14 shows in vivo NIR Raman spectra from one normal and one abnormal site in patient 2. Significant silica peaks are observed at 626 and 818 cm$^{-1}$ which obscure any tissue peaks in this region.
Figure 18A:
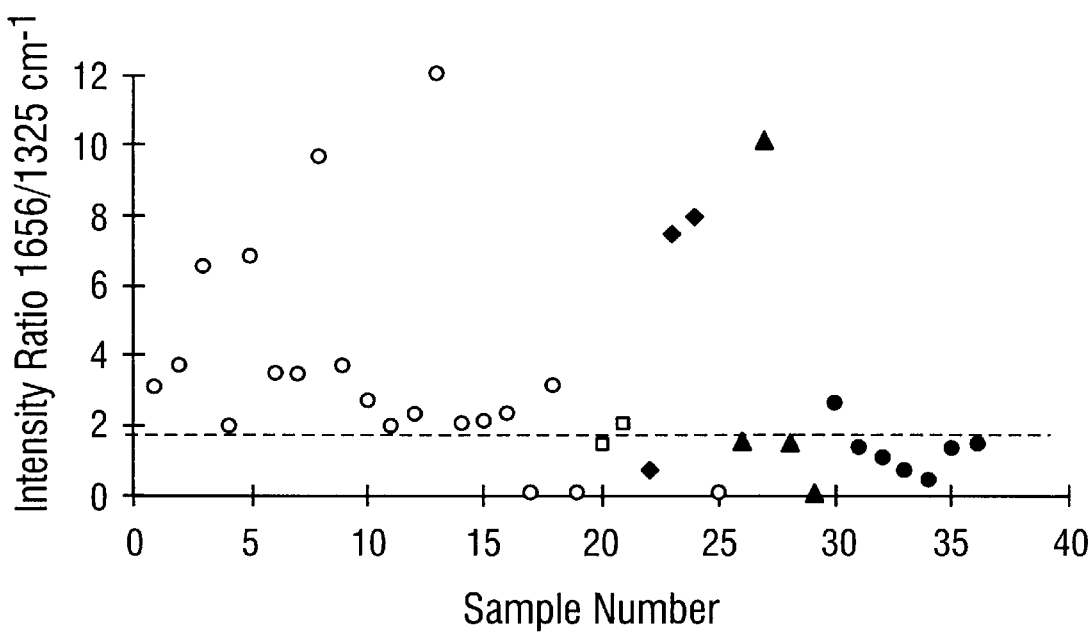
FIGS. 18A and 18B.
Figure 18B:
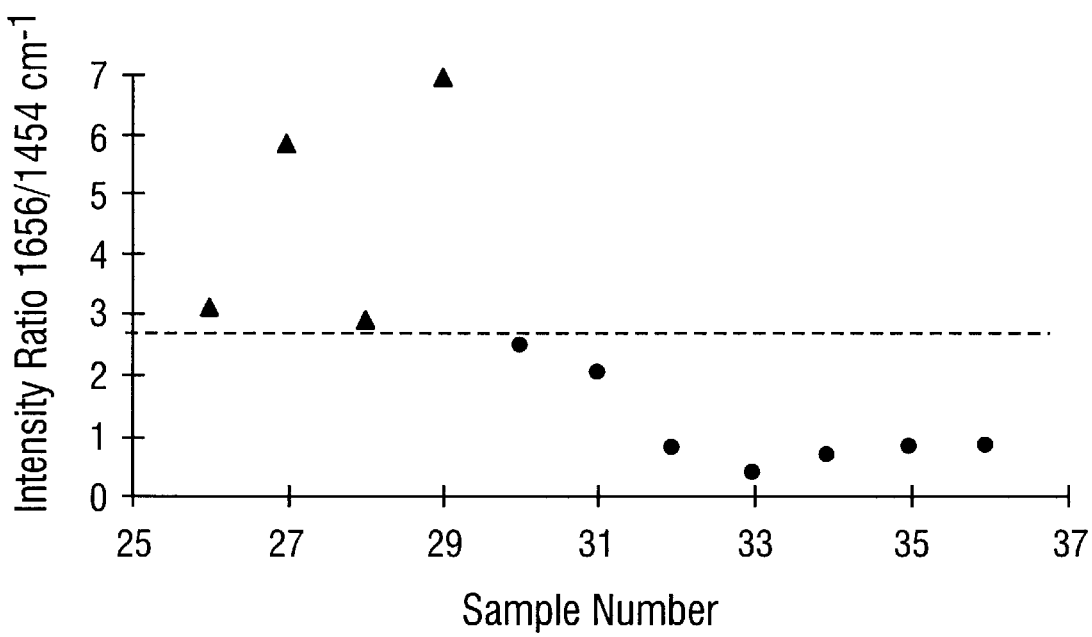

FIG. 14 shows the Raman spectra of a normal and SIL site investigated in patient 2. Examination of the spectra between 900 and 1800 $cm^{-1}$ indicate that tissue peaks are observed at 934, 1066, 1147, 1175, 1204, 1252, 1321, 1343, 1401, 1452, 1570 and 1659 $cm^{-1}$. The peak at 936 $cm^{-1}$ is present with about equal intensity in both the normal and SIL spectra of this patient. The intensity of the glucose phosphate peak at 1066 $cm^{-1}$ is greater in the SIL spectrum as compared to the normal in patient 2. The intensity of the 1321 $cm^{-1}$ band is similar in the normal as well as the abnormal spectra in this patient. However, the unnormalized ratio of intensities at 1659 and 1321 $cm^{-1}$ is less than 1.9, classifying the sample as a SIL using an in vitro algorithm, as shown in FIG. 18A. In addition, the unnormalized ratio of intensities at 1659 and 1452 $cm^{-1}$, is less than 1, classifying the sample as a high grade lesion using an in vitro algorithm in FIG. 18B which agrees with the histology.

Figure 15:
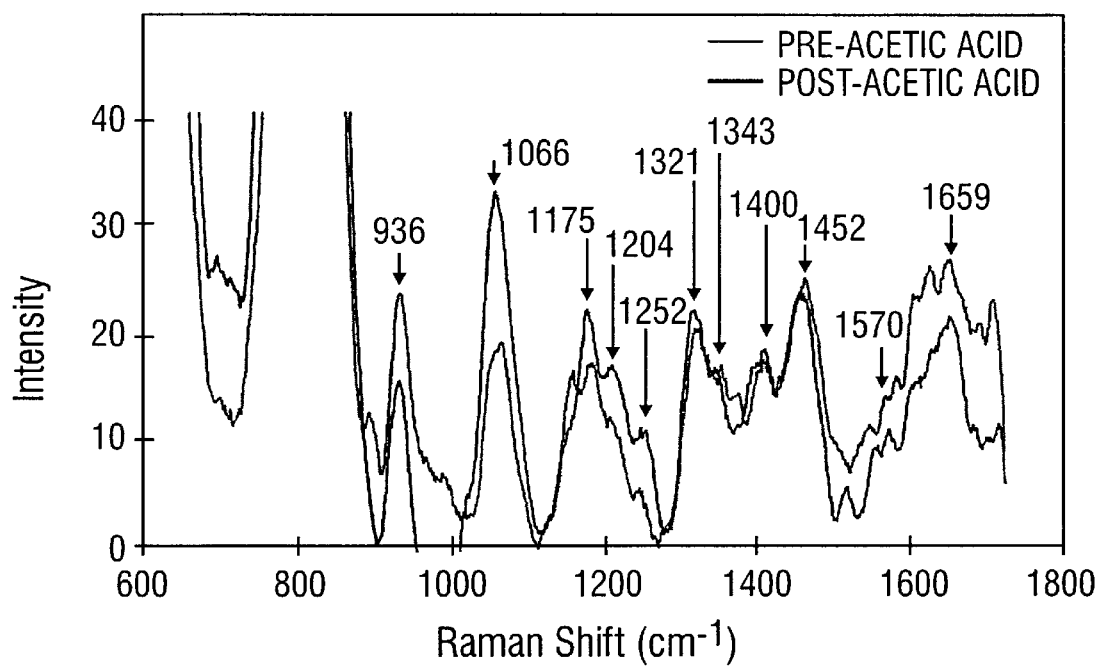
FIG. 15 shows in vivo NIR Raman spectra of the cervix before and after applying acetic acid on the same site in patient 3.

Two Raman spectra were obtained in patient 3 from the same normal site; one before applying acetic acid and one after applying acetic acid, a standard procedure during colposcopy. Acetic acid causes abnormal areas to become white which enhances lesion separation. To ascertain that application of acetic acid does not affect tissue Raman spectra, pre-acetic acid and post-acetic acid spectra were compared (FIG. 15).

A trace of the in vitro peak at 978 $cm^{-1}$ (not shown) in the pre-acetic spectra which is lost in spectra acquired post-acetic acid. An increase in the intensity of the post-acetic acid peak at 1066 $cm^{-1}$, attributed to glucose 1-phosphate is the primary spectral variation. The peak at 1147 (not shown) $cm^{-1}$ has a lower intensity in the post-acetic acid spectrum. An additional peak at 1520 $cm^{-1}$ (not shown) is also observed in the post-acetic acid spectrum. However, this peak is not consistently observed in all post-acetic acid Raman spectra obtained from normal sites in other patients.

Figure 16:
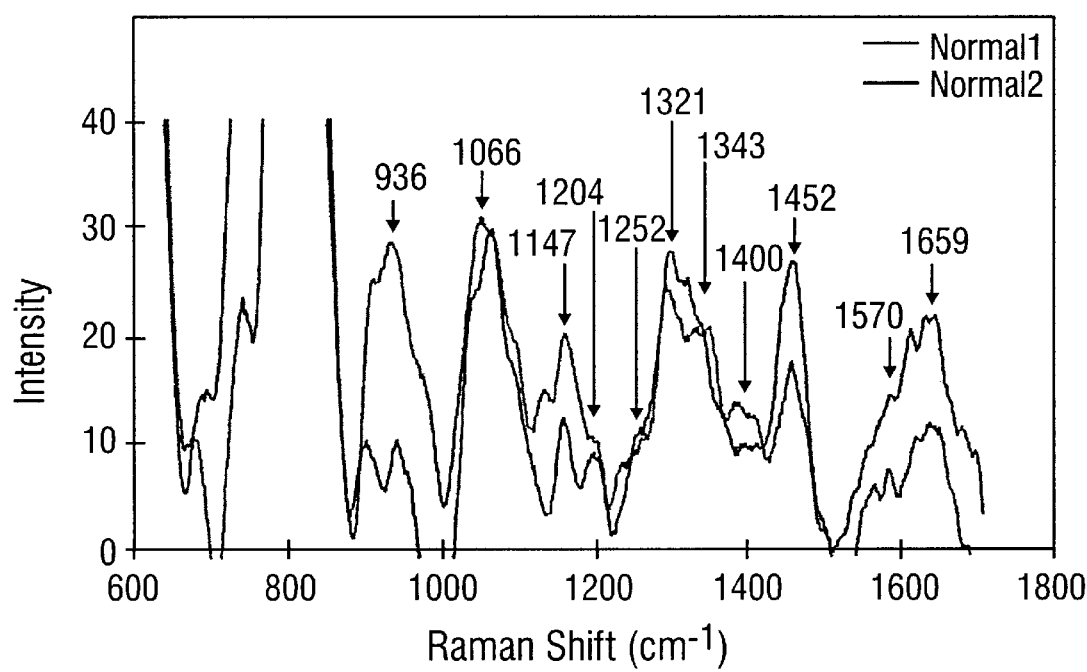
FIG. 16 shows in vivo NIR Raman spectra from two different sites in patient 3 to demonstrate intra-patient variability.

To assess the intra-patient variability in cervical tissue Raman spectra acquired in vivo, two different normal sites were investigated in patient 4 (FIG. 16). Comparison of the Raman spectra from the two sites show some variation in the intensity of several peaks but the ratio of intensities between peaks remains the same. For example, the ratio of intensities at 1659 and 1452 $cm^{-1}$ is 0.72 in normal 1 and 0.77 in normal 2. In addition, the peak at 978 $cm^{-1}$ is present in normal 2 but is absent in normal 1.

Discussion: The in vivo Raman spectra observed here appear similar to in vitro Raman spectra obtained with a bandpass filter placed before the excitation fiber. Comparison of the Raman peaks observed in cervical tissue spectra acquired in vivo and in vitro show similar primary Raman peaks. A Raman peak at 934 $cm^{-1}$ is observed in all in vivo spectra, but is not observed in vitro. On the other hand, in vitro Raman spectra showed a peak at 978 $cm^{-1}$ which is not consistently observed in vivo. The in vivo peak at 934 $cm^{-1}$ was previously reported by Liu et al. (31) in normal and "benign" samples, "benign" including SILs. Comparison to the chromophore spectra indicates that this peak may be due to the presence of glucose. Glycogen also has a peak at 940 $cm^{-1}$. The peak at 978 $cm^{-1}$ was earlier assigned to glucose-1-phosphate. Glucose-1-phosphate is an intermediate product in the glucose—glycogen cycle (32). Glycogen is abundantly present in normal cervical epithelium. This may explain the presence of signal arising from these components and the variability in their presence. The amide bands at 1252 and 1659 $cm^{-1}$ are not as prominent in vivo as they are in vitro. However, the 1659 $cm^{-1}$ amide peak appears to be diagnostically relevant. The nucleic acid peak at 1325 $cm^{-1}$ is much more intense in vivo. All other Raman peaks appear similar in vivo as well as in vitro.

The unpaired ratio algorithms developed in vitro (Appendix I) correctly classify the one diseased sample in patient 2. It is interesting to note that this lesion was incorrectly identified as a human papilloma viral infection under colposcopic impression by the participating practitioner. This indicates in vivo Raman spectra has the potential to provide the diagnostic information necessary to distinguish between SILs and non-SILs.

In vivo tissue Raman spectra measured here still display an overlap of silica and tissue Raman signal, indicated by the intense Raman peaks at 626 and 818 $cm^{-1}$. It is hypothesized that although some contribution to this interfering signal may arise from the fibers and optics used in the probe, the primary source of signal is the quartz shield used as a barrier between the probe and the sample. A thinner quartz shield may reduce this background signal but will not eliminate it. Most known materials that could potentially be used as a window, such as sapphire and transparent Teflon, have a distinct Raman signal that would be detected by the probe. However, it should be noted that the Raman peaks of these materials are much narrower than that of quartz or tissue, which may allow its subtraction without loss of tissue peaks. Hence these materials may provide an alternative to quartz as a probe window. A probe built with a removable window would allow several different materials to be tested, in accordance with the teachings provided herein, before making an appropriate selection.

A possible improvement in the clinical Raman system is the use of a higher power laser. Although the use of a higher power laser was discarded earlier, the laser power at the tip of the probe in this study was 15 mW with a spot size of about 900 mm, resulting in an increase in calculated temperature of only 1.5° C. after 5 minutes. Given the spot size at the sample from the Raman probe, a laser power of up to 80 mW could be used with a corresponding rise in cervical tissue temperature of 6° C. A higher power laser in conjunction with the CCD camera could improve the integration time to about 15 seconds (Table 1, column 7).

VI. References

The following references, to the extent that they provide exemplary experimental details or other information supplementary to that set forth herein, are incorporated by reference:

1. Cancer Facts and Figures, American Cancer Society, 12 (1995).

2. G. H. Anderson, *British Med. J,* 296, 975 (1988).

3. T. C. Wright et al. "Cervical Intraepithelial Neoplasia" in *Blaustein's Pathology of the Female Genital Tract*, (Springer-Verlag, New York, 1994), p. 156.

4. L. G. Koss, *J. Am. Med. Assoc.*, 261, 737 (1989).

5. M. F. Mitchell, "Diseases of the Female Lower Genital Tract" in *Operative Gynecology*, (W. B. Saunders, Philadelphia, 1993), p. 231.

6. B. A. Miller, L.A.G. Flies, B. F. Hankey, Kosary, A. Harras, S. S. Devesa, B. K. Edwards, *Seer Cancer Statistics Review* 1973–1990, (US Department of Health and Human Services, Bethesda, 1993), p. v.1.

7. R. R. Alfano, G. C. Tang, A. Pradhan, W. Lam, D.S.C. Choy, A. Opher, *IEEE Journal of Quantum Electronics*, QE-23, 1806 (1987).

8. J. Hung, S. Lam, J. C. LeRiche, B. Palcic, *Lasers Surg. Med.*, 11, 99 (1991).

9. R. M. Cothren, R. Richards-Kortum, M. V. Sivak, M. Fitzrnaurice, R. P. Rava, G. A. Boyce, G. B. Hayes, M. Doxtader, R. Blackman, T. Ivanc, M. S. Feld, R. E. Petras. *Gastrointest. Endoscop.*, 36, 105 (1990).

10. W. S. Glassman, C. H. Liu, G. C. Tang, S. Lubicz, R. R. Alfano, *Lasers in Life Sciences*, 5, 49 (1992).

11. W. Lohmann, J. Musmann, C. Lohmann, W. Kunzel, *Euro. J. Obstet. Gynecol. Reprod. Biol.*, 31, 249 (1989).

12. N. Ramanujam, M. F. Mitchell, A. Mahadevan, S. Thomsen, R. Richards-Kortum, *Proc. Nat'l Acad. Sci. USA*, 91, 10193 (1994).

13. D.C.B. Redd, Z. C. Feng, K. T. Yue, T. S. Gansler, *Appl. Spectr.*, 47, 787 (1993).

14. M. Motamedi, R. J. Erckens, M. J. Goetz Jr., J. P. Wicksted, G. L. Cote, W. F. March, *SPIE*, 2388, (1995).

15. Y. Ozaki, A. Mizuno, *SPIE*, 1403, (1990).

16. C. H. Lui, B. B. Das, W. L. Sha Glassman, G. C. Tang, K. M. Yoo, H. R. Zhu, D. L. Akins, S. S. Lubicz, J. Cleary, R. Prudente, E. Cellmer, A. Caron, R. R. Alfano, *J. Photochem. Photobiol. B: Biol.*, 16, 187 (1992).

17. M. S. Feld, J. F. Brennan III, A. Berger, R. Manoharan, Y. Wang, *SPIE*, 2388, 99 (1995).

18. R. R. Alfano, C. H. Lui, W. L. Sha, H. R. Zhu, D. L. Akins, J. Cleary, R. Prudente, E. Cellmer, *Lasers in Life Sci.*, 4, 23 (1991).

19. J. F. Brennan III, T. J. Romer, Y. Wang, A. M. Tercyak, R. S. Lees, R. R. Dasari, J. R. Kramer, M. S. Feld, *SPIE*, 2388, 105 (1995).

20. J. J. Baraga, M. S. Feld, R. P. Rava, *Appl. Spectr.*, 46, 187 (1992).

21. Y. Wang, R. L. McCreery, *Anal Chem*, 61, 2647 (1989).

22. A. Mahadevan, N. Ramanujam, M. F. Mitchell, A. Malpica, S. Thomsen, R. Richards-Kortum, *SPIE*, 2388,110 (1995).

23. M. A. Schulze, *Doctoral Dissertation*, University of Texas at Austin (1994).

24. C. J. Frank, R. L. McCreery, D. C. Redd. "Raman Spectroscopy of Normal and Diseased Human Breast Tissues,." *Analytical Chemistry*, 67(5), 777–783 (1995).

25. A. J. Berger, I. Itzkan, M. S. Feld, "Noninvasive Concentration Measurements of Dissolved Analytes in Human Whole Blood by Raman Spectroscopy," *Photochemistry and Photobiology*, Suppl. (1995).

26. N. T. Yu, J.F.R. Kuck Jr. C. C. Askren. "Laser Raman Spectroscopy of the Lens In Situ, Measured in an Anesthetized Rabbit," *Current Eye Research*, 1(10), 615–618 (1982).

27. B. Schrader, S. Keller, T. Loechte, S. Fendel, D. S. Moore, A. Simon and J. Sawatzki. "NIR FT Raman Spectroscopy in Medical Diagnosis," *J. Mol. Structure*, 348, 293–296 (1995).

28. A. C. Williams, B. W. Barry, H. G. Edwards. D. W. Farwell. "A Critical Comparison of Some Raman Spectroscopic Techniques for Studies of Human Stratum Comeum," *Pharm. Res.*, 10(11), 1642–1647 (1993).

29. E. L. Dereniak, D. G. Crowe. *Optical Radiation Detectors*, John Wiley & Sons, New York (1984).

30. M. L. Myrick, S. M. Angel and R. Desiderio. "Comparison of Some Fiber Optic Configurations for Measurement of Luminescence and Raman Scattering," *Applied Optics*, 29(9), 1333–1344 (1990).

31. C. H. Liu, B. B. Das, W. L. Sha Glassman, G. C. Tang, K. M. Yoo, H. R. Zhu, D. L. Akins, S. S. Lubicz, J. Cleary, et al. "Raman, Fluorescence and Time-Resolved Light Scattering as Optical Diagnostic Techniques to Separate Diseased and Normal Biomedical Media," *J. Photochem. Photobiol. B: Biol.*, 16, 187–209 (1992).

32. S. E. Nave, P. E. O'Rourke, W. R. Toole, "Sampling probes enhance remote chemical analyses," *Laser Focus World*, 31(12) (1995).

APPENDIX I: PRINCIPAL COMPONENTS
Algorithm for entire spectrum:

| Spectra # | Sample | Sample Type | PC2 | PC3 | PC6 | PC10 | PC11 | PC22 |
|---|---|---|---|---|---|---|---|---|
| 1 | 205 | Normal | 1.543567 | 6.348307 | −11.5265 | −3.85568 | −0.35106 | 2.074359 |
| 2 | 206 | Normal | 0.675776 | 7.682844 | −3.1951 | −1.88044 | 2.758224 | 1.411211 |
| 3 | 208 | Normal | 3.023087 | 8.267263 | 4.48342 | −2.66354 | 1.1581 | 1.350089 |
| 4 | 210 | Normal | 2.795302 | 7.981375 | −8.48441 | −4.54498 | 0.099619 | 2.612589 |
| 5 | 211 | Normal | 0.584463 | 4.663981 | −7.7627 | −3.60148 | 0.411765 | 2.108621 |
| 6 | 212 | Normal | 1.145271 | 4.260482 | −6.33389 | −1.98227 | 0.475544 | 0.919255 |
| 7 | 214 | Normal | 1.596303 | 4.153986 | −6.00904 | −2.25171 | 0.054386 | 1.753455 |
| 8 | 216 | Normal | 10.24184 | 2.724157 | −8.21057 | −1.598 | 0.794613 | −0.00061 |
| 9 | 218 | Normal | 3.184082 | 9.355728 | −8.06321 | −1.25937 | −0.40054 | 1.947161 |
| 10 | 220 | Normal | −5.27235 | 7.425923 | −9.02191 | −0.50585 | −0.95993 | 2.127007 |
| 11 | 224 | Normal | 3.014144 | 6.76035 | −5.01533 | −2.0569 | −1.50138 | 1.871378 |
| 12 | 226 | Normal | 0.920394 | 10.87519 | 4.232368 | −3.38003 | 0.24081 | 2.185378 |
| 13 | 228 | Normal | 12.53544 | 1.864631 | −8.27384 | −2.42545 | 0.048752 | 1.348167 |
| 14 | 230 | Normal | 2.832068 | 5.122482 | −2.88442 | −0.8595 | −0.18846 | 1.910948 |
| 15 | 234 | Normal | 4.334318 | 4.948299 | −9.9853 | −3.10534 | 5.583419 | 1.500318 |
| 16 | 235 | Normal | 1.524456 | −1.26834 | −3.73109 | −7.37921 | −0.67991 | 2.572718 |
| 17 | 236 | Normal | −1.1622 | 4.14058 | −7.10158 | −5.46803 | 1.238561 | 3.035817 |
| 18 | 238 | Normal | 4.743856 | −0.26435 | −6.10788 | −3.29107 | 1.105041 | 2.248523 |
| 19 | 240 | Normal | 1.776385 | −2.27109 | −4.4548 | 0.072194 | −0.44392 | 3.320742 |
| 20 | 217 | Metaplasia | 1.752317 | 5.937658 | −5.67794 | −1.90016 | 0.085876 | 0.403281 |
| 21 | 219 | Metaplasia | 3.278303 | 3.265713 | −6.14614 | −5.19454 | 3.596982 | 2.192891 |
| 22 | 221 | Inflammation | 4.702379 | 9.837001 | −12.0999 | −2.75127 | −0.9469 | 1.738687 |
| 23 | 222 | Inflammation | 3.296747 | 8.903145 | −2.01524 | −6.28015 | −1.65013 | 1.303856 |
| 24 | 223 | Inflammation | 6.006808 | 9.880243 | −7.69385 | −0.1685 | 3.816562 | 3.699493 |
| 25 | 232 | Inflammation | 0.569056 | 4.714893 | −7.50604 | −6.21167 | 3.826786 | 0.607226 |
| 26 | 207 | Low Grade SIL | 0.561945 | 5.602499 | −4.57135 | −2.37876 | 1.373767 | 0.890093 |
| 27 | 227 | Low Grade SIL | −0.80711 | 5.653207 | −5.48179 | −1.70089 | 2.738444 | 1.496372 |
| 28 | 237 | Low Grade SIL | 2.224185 | −4.41891 | −6.95601 | −1.162 | 0.198199 | 1.485232 |

-continued

APPENDIX I: PRINCIPAL COMPONENTS
Algorithm for entire spectrum:

| Spectra # | Sample | Sample Type | PC2 | PC3 | PC6 | PC10 | PC11 | PC22 |
|---|---|---|---|---|---|---|---|---|
| 29 | 239 | Low Grade SIL | −2.25774 | −0.10565 | −6.79854 | −0.49424 | −1.33124 | 2.20795 |
| 30 | 209 | High Grade SIL | 2.533221 | 6.647742 | −5.78931 | −2.68879 | 1.717242 | 2.475575 |
| 31 | 213 | High Grade SIL | −0.0895 | 2.906415 | −6.00665 | −2.58069 | 0.035438 | 0.931105 |
| 32 | 215 | High Grade SIL | −0.7773 | 3.910833 | −4.02586 | 0.626846 | 3.715693 | 2.181627 |
| 33 | 225 | High Grade SIL | 2.272768 | 1.092567 | −4.60775 | −4.32622 | 1.494353 | 0.333735 |
| 34 | 229 | High Grade SIL | −22.5061 | 5.707699 | −8.81068 | −3.32392 | 1.213121 | 1.259896 |
| 35 | 231 | High Grade SIL | 0.676066 | 1.891038 | −2.50145 | −2.54445 | 3.625361 | 2.393629 |
| 36 | 233 | High Grade SIL | −0.45883 | −1.0537 | −3.62572 | 0.717738 | 1.235546 | 0.202693 |

Algorithm for eight intensities:

| Spectra # | Sample # | Sample Type | PC1 | PC2 |
|---|---|---|---|---|
| 1 | 205 | Normal | 1.1458848 | −3.1255965 |
| 2 | 206 | Normal | 1.1901133 | −2.5139951 |
| 3 | 208 | Normal | 1.834169 | −3.0472687 |
| 4 | 210 | Normal | 1.9385339 | −3.0518833 |
| 5 | 211 | Normal | 1.2691274 | −2.3443378 |
| 6 | 212 | Normal | 1.3146177 | −1.9820707 |
| 7 | 214 | Normal | 1.2224279 | −2.204537 |
| 8 | 216 | Normal | 6.8626189 | −2.7992257 |
| 9 | 218 | Normal | 3.2312321 | −4.2633651 |
| 10 | 220 | Normal | 5.0182456 | −1.6072238 |
| 11 | 224 | Normal | 4.9603838 | −2.0805216 |
| 12 | 226 | Normal | 6.2036942 | −2.5109298 |
| 13 | 228 | Normal | 9.2114828 | −2.9830391 |
| 14 | 230 | Normal | 5.2514816 | −2.8088963 |
| 15 | 234 | Normal | 5.9115984 | −2.7809312 |
| 16 | 235 | Normal | 4.1752079 | −1.3949086 |
| 17 | 236 | Normal | 4.3566001 | −0.048286078 |
| 18 | 238 | Normal | 6.693896 | −1.6661062 |
| 19 | 240 | Normal | 4.9669454 | −1.440043 |
| 20 | 217 | Metaplasia | 4.1113339 | −1.4176762 |
| 21 | 219 | Metaplasia | 5.3999799 | −1.2857701 |
| 22 | 221 | Inflammation | 5.7796724 | −3.7633856 |
| 23 | 222 | Inflammation | 6.3565578 | −2.4393958 |
| 24 | 223 | Inflammation | 5.7032673 | −2.8104215 |
| 25 | 232 | Inflammation | 3.9806831 | −2.5245282 |
| 26 | 207 | Low Grade SIL | 1.4079334 | −2.4003275 |
| 27 | 227 | Low Grade SIL | 3.5186656 | −1.4919014 |
| 28 | 237 | Low Grade SIL | 4.7394294 | −0.33047979 |
| 29 | 239 | Low Grade SIL | 5.2064229 | −0.94494107 |
| 30 | 209 | High Grade SIL | 2.3771245 | −2.6865663 |
| 31 | 213 | High Grade SIL | 0.70798509 | −1.3977078 |
| 32 | 215 | High Grade SIL | 3.0091378 | −0.80670927 |
| 33 | 225 | High Grade SIL | 4.3683959 | −0.78866125 |
| 34 | 229 | High Grade SIL | 4.0888702 | 0.79444495 |
| 35 | 231 | High Grade SIL | 3.1164238 | −0.86678825 |
| 36 | 233 | High Grade SIL | 3.8430913 | −0.36249117 |

What is claimed is:

1. An optical probe for in vivo examination comprising:
   (a) a probe body having an optical opening at one end thereof;
   (b) an excitation leg disposed in the probe body, said excitation leg having an optical axis;
   (c) a filter for eliminating all but a selected excitation wavelength, disposed in the excitation leg, in operable relation to the optical axis of said excitation leg;
   (d) a collection leg disposed in the probe body, said collection leg having an optical axis;
   (e) a mirror in operable relation to said optical axis of said excitation leg.

2. The optical probe of claim 1, wherein said excitation and collection legs are separate.

3. The optical probe of claim 1, wherein said excitation leg is comprised of optical excitation fibers and said collection leg is comprised of optical collection fibers.

4. The optical probe of claim 3, wherein said excitation leg and said collection leg are disposed longitudinally in said probe body.

5. The optical probe of claim 4, wherein said mirror establishes an optical path from said optical axis of said excitation leg to said optical opening.

6. The optical probe of claim 1, wherein said excitation leg comprises a focusing lens.

7. The optical probe of claim 6, wherein said filter is disposed in operable relation to said focusing lens.

8. The optical probe of claim 1, wherein said collection leg comprises a focusing lens.

9. The optical probe of claim 8, wherein said collection leg comprises a filter in operable relation to said focusing lens.

10. The optical probe of claim 9, further comprising a collimating lens, in operable relation to said optical opening.

11. The optical probe of claim 10, wherein said collimating lens is about 8 mm in diameter and blocks light having an OD of greater than about 6.

12. The optical probe of claim 7, wherein said filter is an interference filter.

13. The optical probe of claim 12, wherein said interference filter is a bandpass filter.

14. The optical probe of claim 13, wherein said bandpass filter is about 3–4 mm in diameter and blocks light with an OD of greater than about 5.

15. The optical probe of claim 9, wherein said filter is a longpass filter.

16. The optical probe of claim 9, wherein said filter is a notch filter.

17. The optical probe of claim 16, wherein said notch filter is a holographic notch filter.

18. The optical probe of claim 17, wherein said holographic notch filter is about 8 mm in diameter.

19. An optical probe for in vivo examination comprising:
   (a) a probe body, wherein the interior of said probe is anodized;
   (b) an optical opening at one end of said probe body;
   (c) an excitation leg disposed in the probe body, said excitation leg having an optical axis;
   (d) a collection leg disposed in the probe body, said collection leg having an optical axis; and
   (e) a mirror in operable relation to said optical axis of said excitation leg.

20. The optical probe of claim 1, further comprising a shield covering said optical opening.

21. The optical probe of claim 20, wherein said shield is comprised of quartz.

22. The optical probe of claim 20, wherein said shield is comprised of sapphire.

23. The optical probe of claim 20, wherein said shield is comprised of transparent Teflon.

24. The optical probe of claim 1, wherein the diameter of said probe is less than 20 mm.

25. The optical probe of claim 3, wherein the number of said collection fibers is 50.

26. The optical probe of claim 3, wherein the size of said collection fibers is 100 μm.

27. An optical probe for in vivo examination comprising:
   (a) a probe body having an optical opening at one end thereof;
   (b) an excitation leg disposed in the probe body, said excitation leg having an optical axis;
   (c) a collection leg disposed in the probe body, said collection leg having an optical axis; and
   (e) a mirror in operable relation to said optical axis of said excitation leg, wherein said mirror is comprised of a polished gold wire.

28. The optical probe of claim 27, wherein said polishing is at a specific angle greater than the critical angle of quartz.

29. The optical probe of claim 1, wherein said mirror is a parabolic mirror.

30. The optical probe of claim 1, wherein said probe body is comprised of carbonized epoxy.

31. An optical probe for in vivo examination comprising:
   (a) a probe body, wherein said probe body is comprised of aluminum;
   (b) an optical opening at one end of said probe body;
   (c) an excitation leg disposed in the probe body, said excitation leg having an optical axis;
   (d) a collection leg disposed in the probe body, said collection leg having an optical axis: and
   (e) a mirror in operable relation to said optical axis of said excitation leg.

32. The optical probe of claim 1, wherein said probe body is encased in heat-shrink tubing.

33. The optical probe of claim 32, wherein the probe optical window comprises a shield.

34. An optical probe for in vivo examination comprising:
   an elongated probe body having an optical window at one end thereof;
   an optical fiber disposed substantially longitudinally in the probe body, the optical fiber having first and second ends;
   an electromagnetic source coupler mounted on the probe body and coupled to the first end of the optical fiber;
   a first focusing lens disposed in the probe body and having an optical axis substantially normal to the second end of the optical fiber;
   an interference filter disposed in the probe body on the optical axis of the first focusing lens;
   a deflecting mirror disposed in the probe body on the optical axis of the first focusing lens, the interference filter being disposed between the first focusing lens and the deflecting mirror;
   an optical fiber bundle disposed substantially longitudinally in the probe body, the optical fiber bundle having first and second ends;
   an electromagnetic receiver coupler mounted on the probe body, the electromagnetic receiver coupler being coupled to the first end of the optical fiber bundle;
   a collimating lens disposed in the probe body and having an optical axis substantially normal to the second end of the optical fiber bundle;
   a holographic filter disposed in the probe body on the optical axis of the collimating lens and substantially normal thereto; and
   a second focusing lens disposed in the probe body and having an optical axis substantially normal to the second end of the optical fiber bundle, the holographic filter being disposed between the collimating lens and the second focusing lens;
   wherein the deflection mirror is angled with respect to the optical axis of the first focusing lens to establish an optical path from the optical axis of the first focusing lens that intersects with the optical axis of the second focusing lens in a region proximate to and outside of the probe optical window.

35. An apparatus for measuring Raman spectra in vivo comprising:
   a probe according to claim 1;
   an electromagnetic radiation generator;
   a Raman spectrum detector; and
   a means for analyzing said spectra in relation to said electromagnetic radiation.

36. The apparatus of claim 35, wherein said generator is a laser.

37. A method for collecting optical data from a sample site in vivo comprising:
   generating excitation electromagnetic energy;
   conducting the excitation energy longitudinally through a probe;
   concentrating the excitation energy during the excitation energy conducting step;
   filtering the excitation energy during the excitation energy conducting step to eliminate all but a predetermined excitation wavelength from the excitation energy;
   deflecting the excitation energy following the concentration and filtering steps onto the sample site;
   conducting emission radiation resulting from the deflecting step longitudinally through the probe;
   expanding the emission radiation during the emission radiation conducting step;
   interference filtering the emission radiation during the emission radiation conducting step and after the expanding step to eliminate the excitation wavelength from the emission radiation;
   concentrating the emission radiation during the emission radiation conducting step and following the interference filtering step; and
   collecting the emission radiation following the concentrating step.

38. The method of claim 37, wherein the probe comprises a window at an end thereof, the window having known fluorescence and Raman signatures, and further comprising the steps of bringing the window into proximity with the tissue site during the collection step, and removing the known fluorescence and Raman signatures from the collected emission radiation.

39. An optical probe for in vivo examination comprising:
   (a) a probe body having an optical opening at one end thereof,
   (b) an excitation leg disposed in the probe body, said excitation leg having an optical axis, and being transparent to a selected excitation wavelength,
   (c) a collection leg disposed in the probe body, said collection leg having an optical axis;
   (d) a filter for filtering said selected excitation wavelength, disposed in the collection leg, in operable relation to the optical axis of said collection leg; and
   (e) a mirror in operable relation to said optical axis of said excitation leg.

* * * * *